(12) United States Patent
Mitchell et al.

(10) Patent No.: US 9,980,486 B2
(45) Date of Patent: May 29, 2018

(54) HERBICIDAL QUINOLINES

(71) Applicant: Syngenta Participations AG, Basel (CH)

(72) Inventors: Glynn Mitchell, Bracknell (GB); Gordon Richard Munns, Bracknell (GB); Matthew Carl Plane, Bracknell (GB); Nicholas Phillip Mulholland, Bracknell (GB)

(73) Assignee: Syngenta Participations AG, Basel (CH)

( * ) Notice: Subject to any disclaimer, the term of this patent is extended or adjusted under 35 U.S.C. 154(b) by 0 days. days.

(21) Appl. No.: 15/509,401

(22) PCT Filed: Sep. 11, 2015

(86) PCT No.: PCT/EP2015/070791
§ 371 (c)(1),
(2) Date: Mar. 7, 2017

(87) PCT Pub. No.: WO2016/038173
PCT Pub. Date: Mar. 17, 2016

(65) Prior Publication Data
US 2017/0251670 A1    Sep. 7, 2017

(30) Foreign Application Priority Data

Sep. 12, 2014 (GB) .................................. 1416111.1

(51) Int. Cl.
| | | |
|---|---|---|
| *C07D 401/12* | (2006.01) | |
| *C07D 401/14* | (2006.01) | |
| *C07D 405/14* | (2006.01) | |
| *C07D 409/14* | (2006.01) | |
| *C07D 413/14* | (2006.01) | |
| *C07D 417/14* | (2006.01) | |
| *A01N 43/713* | (2006.01) | |
| *A01N 43/653* | (2006.01) | |
| *A01N 43/54* | (2006.01) | |
| *A01N 43/80* | (2006.01) | |

(52) U.S. Cl.
CPC .......... *A01N 43/713* (2013.01); *A01N 43/653* (2013.01); *A01N 43/80* (2013.01); *C07D 401/12* (2013.01); *C07D 401/14* (2013.01); *C07D 405/14* (2013.01); *C07D 409/14* (2013.01); *C07D 413/14* (2013.01); *C07D 417/14* (2013.01)

(58) Field of Classification Search
CPC .. C07D 401/12; C07D 401/14; C07D 405/14; C07D 409/14; C07D 411/14; C07D 413/14; C07D 417/14; A01N 43/713; A01N 43/653; A01N 43/54
See application file for complete search history.

(56) References Cited

U.S. PATENT DOCUMENTS

| | | | |
|---|---|---|---|
| 2015/0216171 A1* | 8/2015 | Ahrens ................ | C07D 413/14 504/105 |
| 2015/0291570 A1* | 10/2015 | Kraus .................. | C07D 401/12 504/273 |
| 2016/0251322 A1* | 9/2016 | Calo .................... | A01N 43/653 504/253 |

FOREIGN PATENT DOCUMENTS

| | | |
|---|---|---|
| WO | 2013092834 A1 | 6/2013 |
| WO | 2014037342 A1 | 3/2014 |
| WO | 2014184074 A1 | 11/2014 |

OTHER PUBLICATIONS

UKIPO Search Report for priority application GB1416111.1 dated May 20, 2015.
Internation Search report for PCT Application No. PCT/EP2015/070791, dated Oct. 19, 2015.

* cited by examiner

*Primary Examiner* — John Pak
(74) *Attorney, Agent, or Firm* — James Cueva

(57) ABSTRACT

The present invention relates to compounds of formula (I), or an agronomically acceptable salt of said compounds wherein $A^{1a}$, $A^{1b}$, $R^1$, $R^2$, $R^3$, $R^4$, $R^5$ and $R^6$ are as defined herein. The invention further relates to herbicidal compositions which comprise a compound of Formula (I), and to their use for controlling weeds, in particular in crops of useful plants.

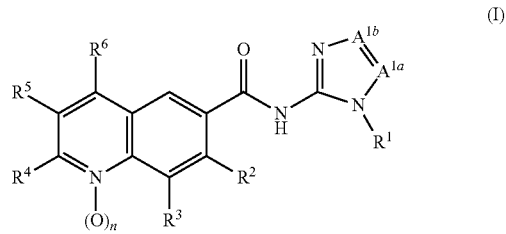

12 Claims, No Drawings

HERBICIDAL QUINOLINES

RELATED APPLICATION INFORMATION

This application is a 371 of International Application No. PCT/EP2015/070791, filed Sep. 11, 2015, which claims priority to GB Application No. 1416111.1, filed Sep. 14, 2014, the contents of which are incorporated herein by reference herein.

The present invention relates to novel herbicidal compounds, to processes for their preparation, to herbicidal compositions which comprise the novel derivatives, and to their use for controlling weeds, in particular in crops of useful plants, or for inhibiting plant growth.

Herbicidal N-(tetrazol-5-yl)- and N-(triazol-5-yl)-arylcarboxamides are disclosed in, for example, WO 2012/028579, WO 2013/092834 and WO 2014/037342. The present invention provides further herbicidal derivatives. Thus, according to the present invention there is provided a compound of Formula (I):

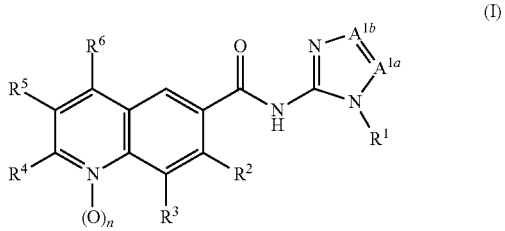

or an agronomically acceptable salt thereof,
wherein:—

$A^{1a}$ and $A^{1b}$ are independently selected from CH and N, wherein $A^{1a}$ and $A^{1b}$ are not both CH;

$R^1$ is selected from the group consisting of $C_1$-$C_6$-alkyl-, $C_1$-$C_6$-alkoxy-$C_1$-$C_3$-alkyl-, $C_1$-$C_6$-haloalkoxy-$C_1$-$C_3$-alkyl-, $C_1$-$C_6$-haloalkyl-, $C_2$-$C_6$-alkenyl-, $C_2$-$C_6$-haloalkenyl-, $C_2$-$C_6$-alkynyl-, $C_2$-$C_6$-haloalkynyl-, heteroaryl- (e.g pyridyl), $(C_3$-$C_7)$-cycloalkyl-, heterocyclyl- (e.g thietanyl, tetrahydropyranyl) and phenyl-, wherein the heteroaryl-, $(C_3$-$C_7)$-cycloalkyl-, heterocyclyl- and phenyl- are optionally substituted by one or more substituents selected from the group consisting of halogen, nitro, cyano, $C_1$-$C_6$-alkyl-, $C_1$-$C_6$-haloalkyl-, $C_3$-$C_6$-cycloalkyl-, $C_1$-$C_6$alkyl-S(O)p-, $C_1$-$C_3$-alkoxy- and $C_1$-$C_6$alkoxy-$C_1$-$C_4$alkyl-;

$R^2$ is selected form the group consisting of $C_1$-$C_6$alkyl-, $C_1$-$C_6$alkoxy-, $C_1$-$C_6$ haloalkyl-, $C_1$-$C_6$haloalkoxy-, $C_1$-$C_6$alkoxy-$C_1$-$C_6$alkyl-, $C_1$-$C_3$alkoxy-$C_2$-$C_3$alkoxy-$C_1$-$C_3$alkyl-, $C_1$-$C_3$alkoxy-$C_{1-3}$-haloalkyl-, $C_1$-$C_3$-alkoxy-$C_1$-$C_3$-alkoxy-$C_2$-$C_3$-haloalkyl-, halogen, cyano, nitro, $C_1$-$C_6$alkyl-S(O)p-, $C_1$-$C_6$haloalkyl-S(O)$_p$—, $C_4$-$C_6$-oxasubstituted-cycloalkoxy-$C_1$-$C_3$-alkyl-, $C_4$-$C_6$-oxasubstituted-cycloalkoxy-$C_1$-$C_3$-haloalkyl-, $(C_1$-$C_3$-alkanesulfonyl-$C_1$-$C_3$ alkylamino)-$C_1$-$C_3$alkyl- and $(C_1$-$C_3$alkanesulfonyl-$C_3$-$C_4$cycloalkylamino)-$C_1$-$C_3$alkyl-;

$R^3$ is aryl or a 5 or 6-membered heteroaryl, the heteroaryl containing one to three heteroatoms each independently selected from the group consisting of oxygen, nitrogen and sulphur, and wherein the aryl or heteroaryl component may be optionally substituted by one or more substituents selected from the group consisting of halogen, $C_1$-$C_6$alkyl-, $C_2$-$C_6$alkenyl-, $C_2$-$C_6$alkynyl-, $C_1$-$C_6$haloalkyl-, $C_1$-$C_6$alkoxy-, $C_1$-$C_6$alkoxy$C_1$-$C_3$alkyl-, $C_1$-$C_6$alkoxy$C_1$-$C_3$alkoxy-, $C_1$-$C_6$haloalkoxy-, $C_1$-$C_6$alkyl-S(O)p-, —$NR^{7a}R^{7b}$, cyano and nitro;

$R^4$ is selected from the group consisting of hydrogen, halogen, hydroxyl, sulfhydryl, $C_1$-$C_6$alkyl-, $C_3$-$C_6$cycloalkyl-, $C_1$-$C_6$haloalkyl-, $C_2$-$C_6$haloalkenyl-, $C_2$-$C_6$alkenyl, $C_3$-$C_6$alkynyl, $C_1$-$C_6$alkoxy, $C_4$-$C_7$cycloalkoxy-, $C_1$-$C_6$haloalkoxy-, $C_1$-$C_6$alkyl-S(O)p-, $C_1$-$C_6$alkoxy-$C_1$-$C_6$alkyl-, $C_1$-$C_6$alkoxy-$C_2$-$C_6$alkoxy- and $C_1$-$C_6$alkoxy-$C_2$-$C_6$alkoxy-$C_1$-$C_6$-alkyl-;

$R^5$ is selected from the group consisting of hydrogen, halogen, $C_1$-$C_6$alkyl- and $C_1$-$C_6$haloalkyl-;

$R^6$ is selected from the group consisting of hydrogen, methyl and halogen;

$R^{7a}$ and $R^{7b}$ are independently selected from the group consisting of hydrogen and $C_1$-$C_6$alkyl or together form a $C_4$-$C_5$ alkylene chain;

n=0 or 1; and
p=0, 1 or 2.

$C_1$-$C_6$alkyl groups include, for example, methyl (Me), ethyl (Et), n- and iso-propyl and n-, sec-, iso- and tert-butyl.

$(C_3$-$C_7)$-cycloalkyl- groups include, for example, cyclopropyl, cyclobutyl, cyclopentyl and cyclohexyl.

Halogen (or halo) encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents present on the same carbon atom may be joined to form a Spiro group. Thus, the methyl groups present in two methoxy substituents may be joined to form a spiro 1,3 dioxolane substituent, for example. Such a possibility is within the scope of the present invention.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$alkyl-S— (alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$alkyl-S(O)— (alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$alkyl-S(O)$_2$— (alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Alkylamino (e.g —$NR^{7a}aR^{7b}$) is, for example, methylamino, ethylamino, n-propylamino, isopropylamino or a butylamino isomer. Dialkylamino is, for example, dimethylamino, methylethylamino, diethylamino, n-propylmethylamino, dibutylamino or diisopropylamino. Preference is given to alkylamino groups having a chain length of from 1 to 4 carbon atoms.

Alkoxyalkyl groups preferably have from 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

In one embodiment of the present invention is a compound of Formula (I) wherein n=0.

In one embodiment of the present invention is a compound of Formula (I) wherein $A^{1a}$ is CH and $A^{1b}$ is N. In another embodiment, $A^{1a}$ is N and $A^{1b}$ is CH. In a particularly preferred embodiment, both $A^1$ and $A^{1b}$ are N.

In another preferred embodiment, $R^1$ is selected from the group consisting of methyl, ethyl and n-propyl (n-Pr), methyl being especially preferred.

In another preferred embodiment, $R^2$ is selected form the group consisting of $C_1$-$C_6$alkyl- (preferably methyl), $C_1$-$C_6$alkoxy- (preferably methoxy-), $C_1$-$C_6$ haloalkyl- (preferably trifluoromethyl-), halogen (preferably chlorine) and $C_1$-$C_6$alkyl-S(O)p- (preferably —$SO_2$-methyl). In a particularly preferred embodiment, $R^2$ is selected from the group consisting of trifluoromethyl, —$SO_2$-methyl and chlorine.

In another embodiment, $R^3$ is an aryl or heteroaryl selected from the group consisting of phenyl, furanyl, thiophenyl, thiazolyl, oxazolyl, isoxazolyl, imidazolyl, thiazolyl, pyrazolyl, isothiazolyl, pyridyl, pyridazinyl, pyrazinyl, pyrimidinyl and triazolyl all of which may be optionally substituted by one or more substituents as described herein. The exact number of optional substituents will be dictated by the nature of the aryl or heteroaryl group, but typically one, two or three substituents may exist. In a preferred embodiment, $R^3$ is selected from the group consisting of phenyl, thiophenyl and pyridyl all of which may be optionally substituted as described herein. In a particularly preferred embodiment, $R^3$ is phenyl optionally substituted by one or more (preferably one, two or three) substituents selected from the group consisting of halogen (especially fluorine and/or chlorine), $C_1$-$C_6$alkyl- (especially methyl), $C_1$-$C_6$haloalkyl- (especially trifluoromethyl), $C_1$-$C_6$alkoxy- (especially methoxy-), $C_1$-$C_6$haloalkoxy- (especially trifluoromethoxy-), $C_1$-$C_6$alkyl-S(O)p- (especially —$SO_2$-methyl), cyano and nitro.

In another preferred embodiment $R^4$ is selected from the group consisting of hydrogen, $C_1$-$C_6$ alkyl- (preferably methyl) and $C_1$-$C_6$ haloalkyl- (preferably trifluoromethyl-). In a most preferred aspect, $R^4$ is hydrogen or methyl.

In another preferred embodiment $R^5$ is hydrogen or halogen (preferably fluorine or chlorine, in particularly fluorine).

In another preferred embodiment $R^6$ is hydrogen or halogen (e.g chlorine), especially hydrogen.

Compounds of Formula (I) may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

Similarly, where there are disubstituted alkenes, these may be present in E or Z form or as mixtures of both in any proportion.

Furthermore, compounds of Formula (I) may be in equilibrium with alternative tautomeric forms. It should be appreciated that all tautomeric forms (single tautomer or mixtures thereof), racemic mixtures and single isomers are included within the scope of the present invention.

The present invention also includes agronomically acceptable salts that the compounds of Formula (I) may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

The compounds of Formula (I) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound according to any one of the previous claims and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The composition of the present may further comprise at least one additional pesticide. For example, the compounds according to the invention can also be used in combination with other herbicides or plant growth regulators. In a preferred embodiment the additional pesticide is a herbicide and/or herbicide safener. Examples of such mixtures are (in which 'I' represents a compound of Formula I). I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fenquinotrione, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazo late, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6). The compounds of the present invention may also be combined with herbicidal compounds disclosed in WO06/024820 and/or WO07/096576.

The mixing partners of the compound of Formula I may also be in the form of esters or salts, as mentioned e.g. in The Pesticide Manual, Fourteenth Edition, British Crop Protection Council, 2006.

The compound of Formula I can also be used in mixtures with other agrochemicals such as fungicides, nematicides or insecticides, examples of which are given in The Pesticide Manual.

The mixing ratio of the compound of Formula I to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula I according to the invention can also be used in combination with one or more safeners. Likewise, mixtures of a compound of Formula I according to the invention with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxy-benzoylsulfamoyl)-benzamide (CAS RN 221668-34-4). Other possibilities include safener compounds disclosed in, for example, EP0365484 e.g N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methyl-aminocarbonyl)amino]benzenesulfonamide.

The safeners of the compound of Formula (I) may also be in the form of esters or salts, as mentioned e.g. in The Pesticide Manual, 14$^{th}$ Edition (BCPC), 2006. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula I to safener is from 100:1 to 1:10, especially from 20:1 to 1:1.

The mixtures can advantageously be used in the above-mentioned formulations (in which case "active ingredient" relates to the respective mixture of compound of Formula I with the safener).

The present invention still further provides a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula I may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

In a preferred embodiment the crop plant is rendered tolerant to HPPD-inhibitors via genetic engineering. Methods of rending crop plants tolerant to HPPD-inhibitors are known, for example from WO0246387. Thus in an even more preferred embodiment the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria, Cenchrus, Lolium, Festuca, Setaria, Eleusine, Sorghum* or *Avena* species.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica, Viola* and *Xanthium*. Weeds can also include plants which may be considered crop plants but which are growing outside a crop area (escapes'), or which grow from seed left over from a previous planting of a different crop (volunteers'). Such volunteers or escapes may be tolerant to certain other herbicides.

The compounds of the present invention can be prepared according to the following schemes.

Scheme 1:-Reaction of an acid chloride with an aminotriazole or an aminotetrazole

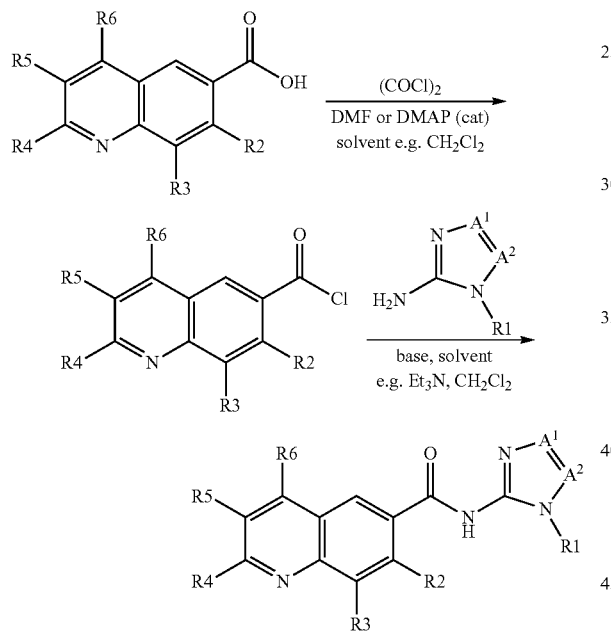

Scheme 2:-Reaction of an activated carboxylic acid with a 1-alkyl-5-aminotetrazole or an aminotriazole:

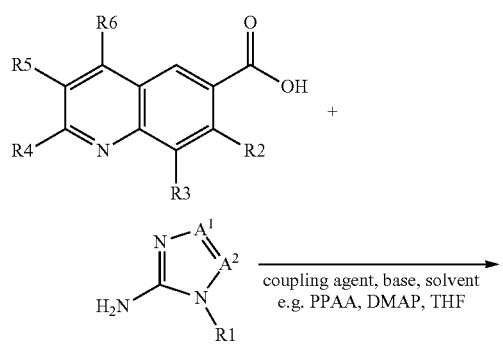

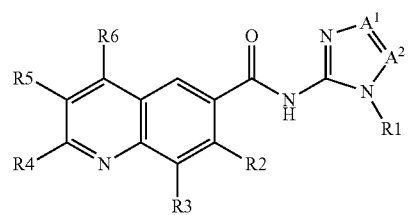

DMAP=4-(dimethylamino) pyridine, PPAA=1-propane-phosphonic acid cyclic anhydride, and the solvent is a non-protic organic solvent such as ethyl acetate, dichloromethane, tetrahydrofuran (THF) or toluene (PhMe).

Scheme 3:-Activation of an acid with N,N'-carbonyldiimidazole (CDI), and reaction with an aminotriazole or an aminotetrazole:

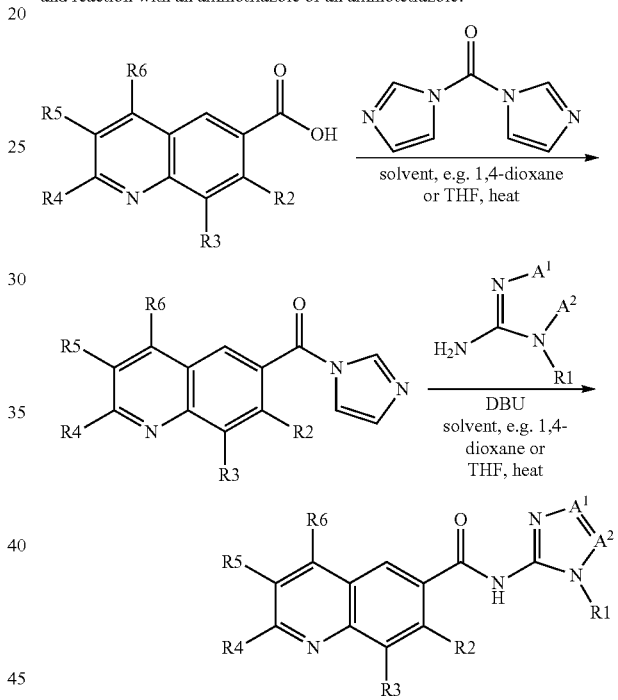

where THF is tetrahydrofuran and DBU is 1,8-diazabicyclo [5.4.0]undec-7-ene.

Scheme 4: Reaction of a carboxylic ester with an aminotriazole or an aminotetrazole:

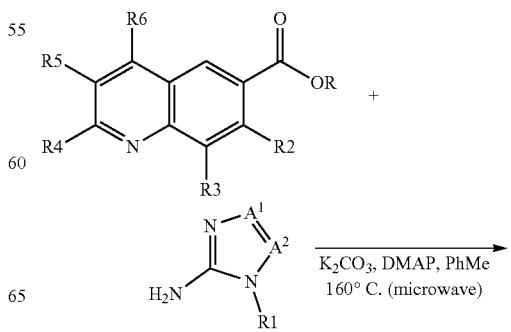

-continued

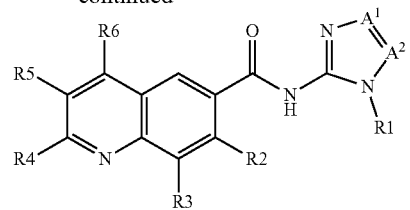

The carboxylic acids and esters can be prepared by known methods, or methods analogous to known methods. Examples of such methods are given below.

Scheme 5: Formation of quinoline ester and acid:

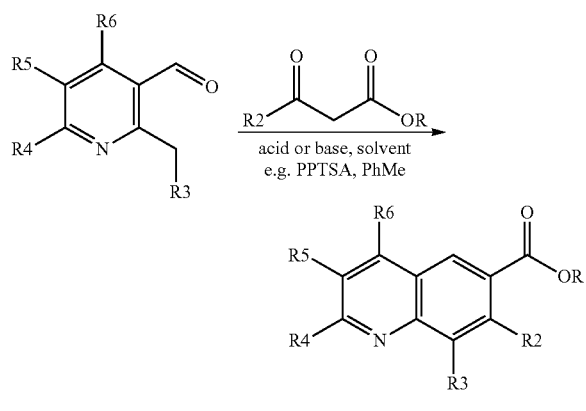

The resulting ester is hydrolysed to the corresponding acid. PPTSA=Pyridinium p-toluenesulfonate Scheme 6: Formation of quinoline amide:

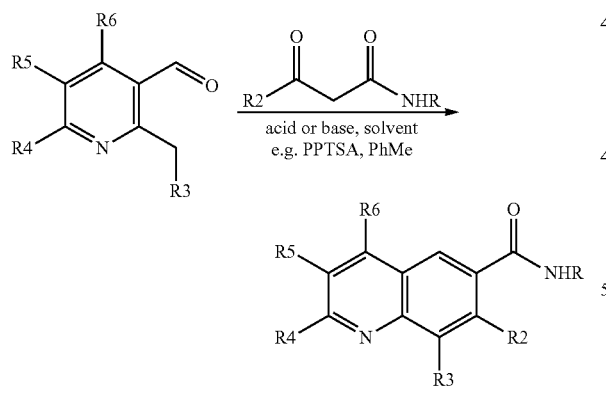

Where R is heteroaryl e.g alkyltetrazole or alkyltriazole.

Scheme 7: Two step quinoline ester formation

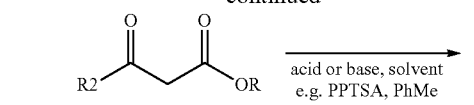
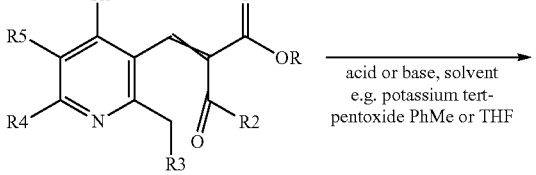
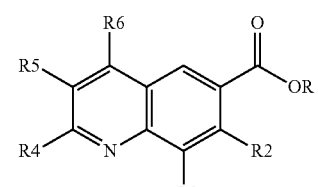

The resulting ester is hydrolysed to the corresponding acid.

Scheme 8:-Two step quinoline ester formation

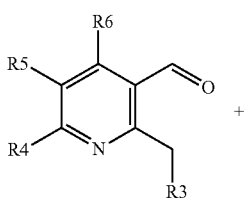

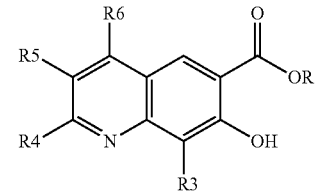

The resulting ester is hydrolysed to the corresponding acid.

Scheme 9:-

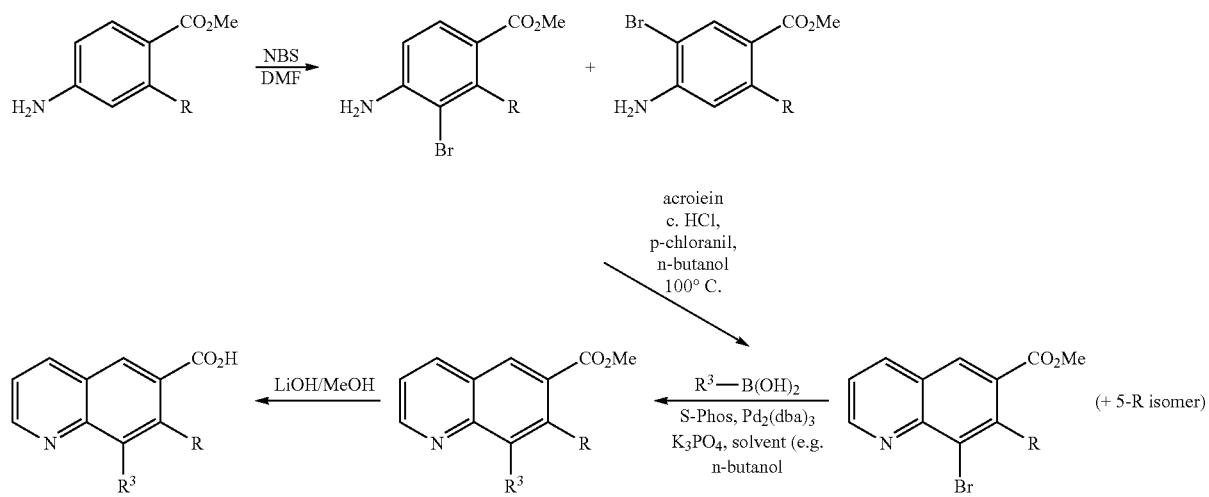

Where R is alkyl or alkoxy, NBS is N-bromosuccinimide, DMF is dimethylformamide, S-Phos is 2-dicyclohexylphosphino-2',6'-dimethoxybiphenyl, and Pd$_2$(dba)$_3$ is tris(dibenzylideneacetone)dipalladium(O).

The carboxylic acids, esters and amides maybe prepared by functional group interconversion at positions (R$^2$, R$^4$, R$^5$, R$^6$) by known methods, or methods analogous to known methods. Examples of such methods are given below.

Scheme 10: Functional group interconversion

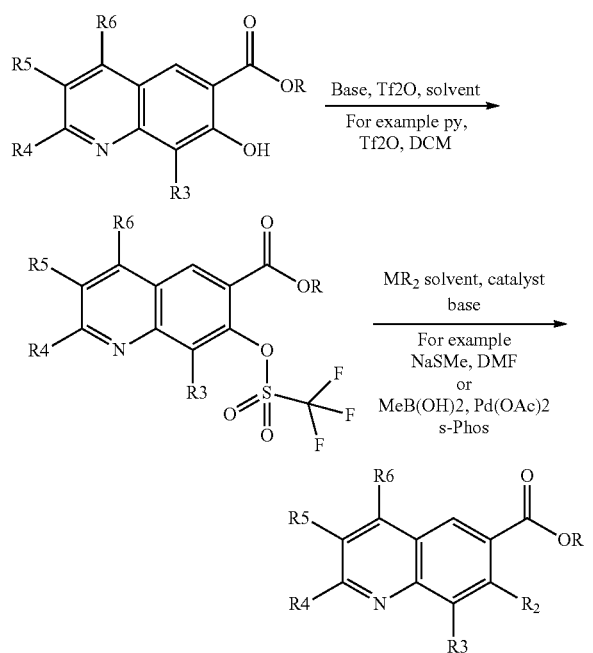

Tf$_2$O=trifluoroacetic anhydride, DCM=dichloromethane, DMF=dimethyl formamide, py=pyridine, S-Phos=2-Dicyclohexylphosphino-2',6'-dimethoxybiphenyl, Where M is a metal or metalloid for example zincate, boronic acid, boronic ester, lithium etc.

Scheme 11: Functional group interconversion.

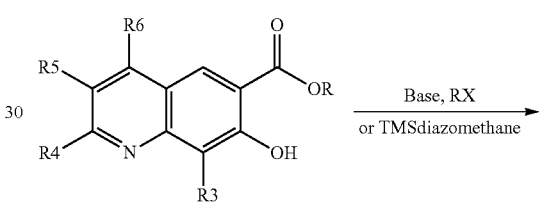

Where R is e.g alkyl-, haloalkyl-, alkoxyalkyl- and where X is a halogen or pseudohalogen. TMS=trimethylsilane.

Scheme 12:-Functional group interconversion

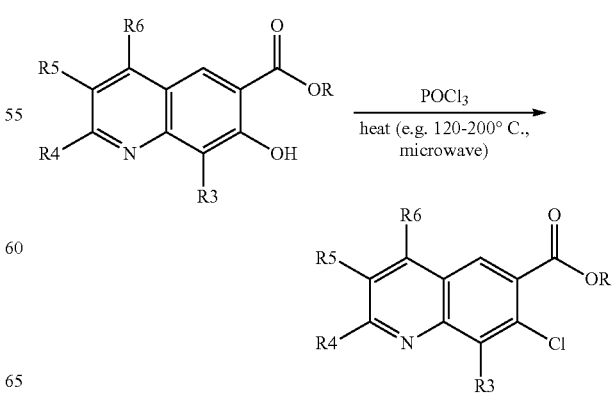

Scheme 13:- Functional group interconversion

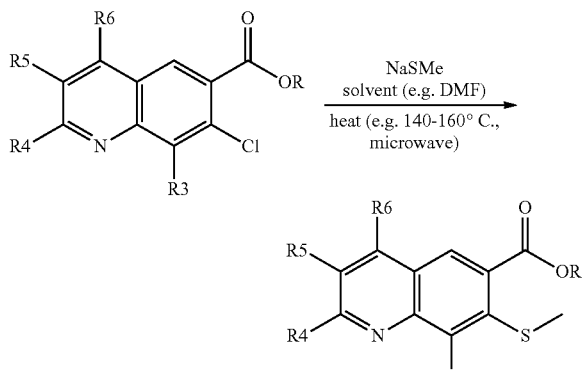

Scheme 14:- Functional group interconversion

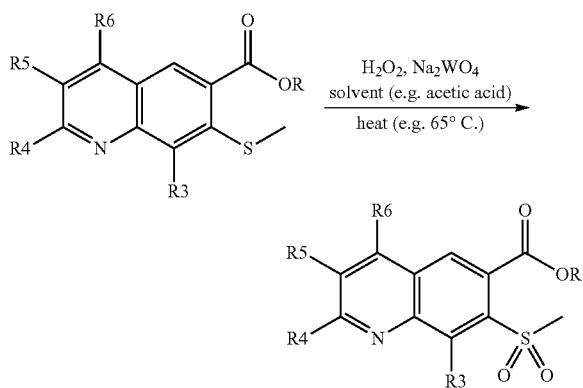

The aldehydes used in Schemes 5, 6, 7 and 8 can be prepared by known methods, or methods analogous to known methods. Examples of such methods are given below.

Scheme 15:

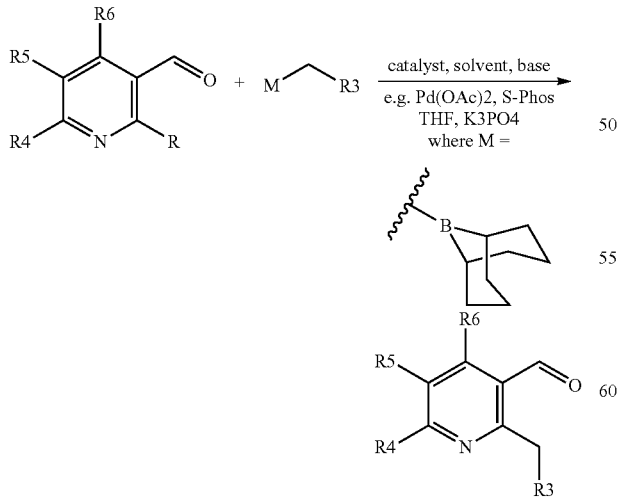

Where M is a metal or metalloid for example zincate, boronic acid, boronic ester, lithium etc. R is a halide (e.g. Cl, Br, I) or pseudohalide (e.g. OMs, OTf, OTs), S-Phos=2-Dicyclohexylphosphino-2',6'-dimethoxybiphenyl.

Scheme 16:

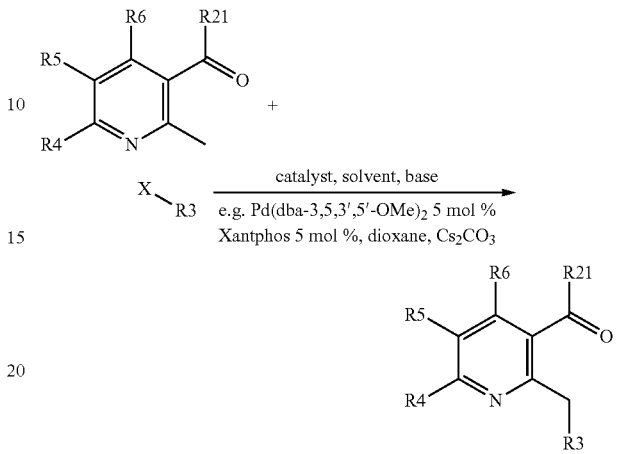

Where $R^{21}$ is hydrogen, OR, SR or $NR_2$ wherein R=e.g alkyl, aryl. X is a halide or pseudohalide. Pd(dba-3,5,3'5'-OMe)$_2$ is Xantphos is 4,5-Bis(diphenylphosphino 9,9-dimethylxanthene. dba=Dibenzylideneacetone Scheme 17:

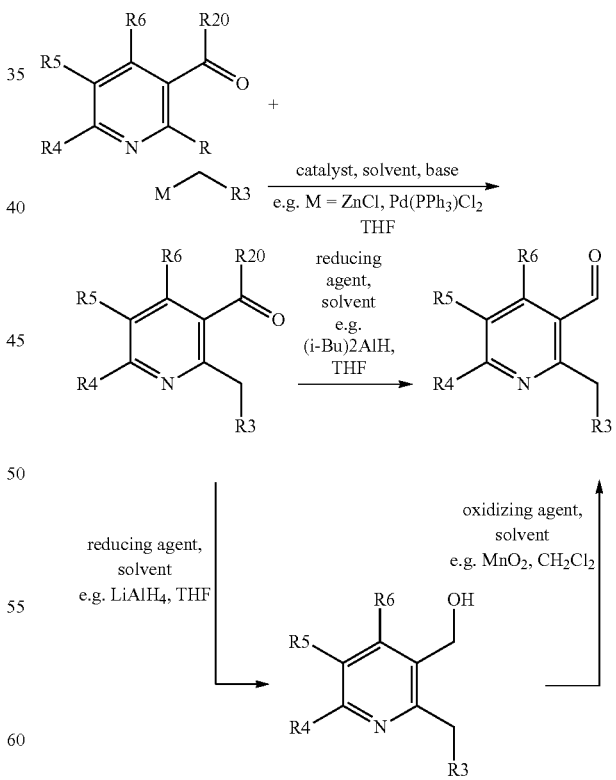

Where $R^{20}$ is hydrogen, OR', SR' or $NR'_2$ wherein R'=e.g alkyl, aryl. R is a halide or pseudohalide. M is a metal or metalloid for example zincate, boronic acid, boronic ester, lithium etc.

Scheme 18: Formation of N-oxides.

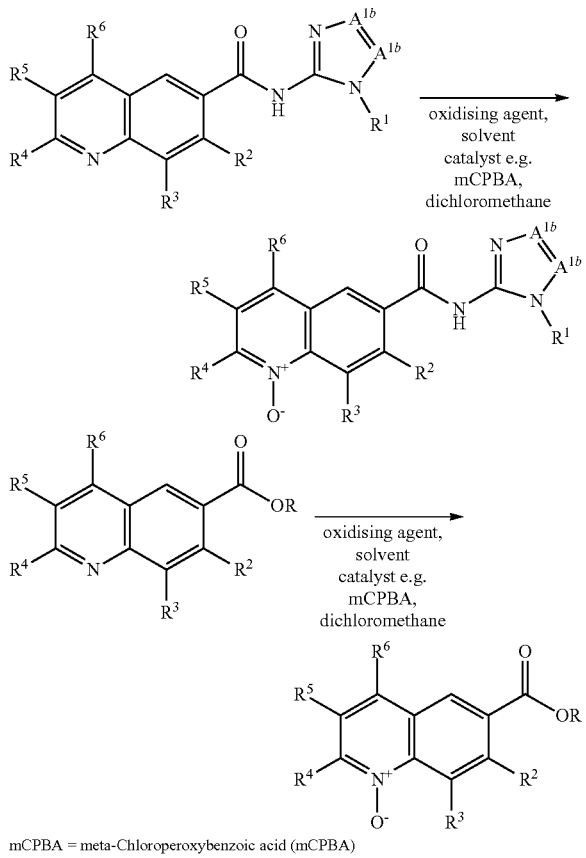

mCPBA = meta-Chloroperoxybenzoic acid (mCPBA)

The following non-limiting examples provide specific synthesis methods for representative compounds of the present invention, as referred to in Table 1 below.

EXAMPLE P1: PREPARATION OF N-(1-METHYLTETRAZOL-5-YL)-8-PHENYL-7-(TRIFLUOROMETHYL)QUINOLINE-6-CARBOXAMIDE (COMPOUND 1.001)

Step 1: Preparation of ethyl 2-benzylpyridine-3-carboxylate

An oven dried 3-neck round bottom flask was charged with bis(triphenylphosphine)palladium(II) dichloride (0.80 g, 1.15 mmol) under nitrogen, followed by neat ethyl 2-chloropyridine-3-carboxylate (4.30 g, 23 mmol) and then a solution of benzyl(bromo)zinc in THF (50 mL, 25 mmol, 0.50 M). The mixture was stirred overnight at room temperature, when LCMS showed formation of the desired product. The mixture was dry loaded onto celite and purified by flash chromatography (silica) eluting with ethyl acetate in iso-hexane, to give ethyl 2-benzylpyridine-3-carboxylate (4.42 g, 80% Yield) as a pale-yellow oil.

1H NMR (400 MHz, CDCl3) δ ppm 8.69 (dd, 1H), 8.16 (dd, 1H) 7.18-7.30 (m, 6H), 4.59 (s, 2H), 4.33 (q, 2H), 1.32 (t, 3H).

Step 2: Preparation (2-benzyl-3-pyridyl)methanol

A solution of ethyl 2-benzylpyridine-3-carboxylate (3.6 g, 15 mmol) in dry THF (70 mL) was cooled in an ice/water bath and treated with a solution of lithium aluminium hydride in THF (11 mL, 22 mmol, 2.0 M). Ten minutes after the addition, the cooling bath was removed and the mixture was stirred at room temperature for 2 hours, when LC showed formation of the desired product. The solution was re-cooled to 0° C. and quenched in succession by the slow addition of water (0.85 ml), 2M NaOH (0.85 ml), and more water (2.5 ml). The mixture was stirred for 15 min, then diethyl ether was added and the mixture was stirred for an additional 15 min. Magnesium sulphate was then added, and after 15 min the mixture was filtered, and the salts were washed with additional diethyl ether. The filtrate was evaporated to dryness—under reduced pressure to give (2-benzyl-3-pyridyl)methanol (2.81 g, 95% Yield) as an off-white solid.

1H NMR (400 MHz, CDCl$_3$) δ ppm 8.52 (dd, 1H), 7.74 (dd, 1H) 7.18-7.30 (m, 6H), 4.67 (d, 2H), 4.24 (s, 2H)

Step 3: Preparation of 2-benzylpyridine-3-carbaldehyde

A stirred mixture of (2-benzyl-3-pyridyl)methanol (2.81 g, 14.1 mmol) and manganese(IV)oxide (12.3 g, 141 mmol) in dichloromethane (28 mL) was heated under reflux for 3 hours, after which additional manganese(IV)oxide (2 g) was added and the mixture was heated for further hour. The reaction was cooled to room temperature, filtered through celite and washed with additional dichloromethane. The filtrate was evaporated under reduced pressure to leave 2-benzylpyridine-3-carbaldehyde (2.39 g, 86% Yield) as an orange oil.

1H (400 MHz, CDCl$_3$) δ ppm 10.34 (s, 1H), 8.77 (dd, 1H), 8.14 (dd, 1H) 7.37 (m, 1H), 7.28-7.19 (m, 5H), 4.61 (s, 2H)

Step 4: Preparation of ethyl 8-phenyl-7-(trifluoromethyl)quinoline-6-carboxylate To a solution of 2-benzylpyridine-3-carbaldehyde (3.0 g, 15.2 mmol) in toluene (30 mL) was successively added ethyl trifluoroacetoacetate (4.45 mL, 30.4 mmol), pyridinium para-toluenesulfonic acid (PPTSA: 382 mg, 1.51 mmol) and the reaction mass was heated under reflux using a Dean-Stark apparatus for 48 h. The cooled reaction mixture was poured into saturated aqueous sodium bicarbonate solution (20 mL) and was extracted with ethyl acetate (20 mL×2). The combined organic layers were then washed with brine (20 mL), dried over sodium sulphate and evaporated to dryness under reduced pressure. The residue was purified by flash chromatography (silica), eluting with 0-30% ethyl acetate in isohexane, to give ethyl 8-phenyl-7-(trifluoromethyl)quinoline-6-carboxylate (3.71 g, 71% Yield) as a pale orange solid.

1H NMR (400 MHz, CDCl$_3$) δ ppm, 9.00 (dd, 1H), 8.25 (dd, 1H), 8.14 (s, 1H), 7.46-7.55 (m, 4H), 7.34-7.40 (m, 2H), 4.46 (q, 2H), 1.43 (t, 3H)

Step 5: Preparation of 8-phenyl-7-(trifluoromethyl)quinoline-6-carboxylic acid

Sodium hydroxide (3.5 g, 88 mmol) was added in one portion to a stirred suspension of ethyl 8-phenyl-7-(trifluoromethyl)quinoline-6-carboxylate (3.71 g, 10.8 mmol) in ethanol (90 mL) and water (30 mL). The reaction mixture was heated under reflux for 5 hours, then cooled to room temperature and left to stand overnight. The reaction was acidified (conc HCl) to pH 3, and the resultant precipitate was washed with water, then air dried to give 8-phenyl-7-(trifluoromethyl)quinoline-6-carboxylic acid (3.18 g, 93% Yield) as an orange solid.

1H NMR (400 MHz, DMSO-d6) δ ppm 13.73 (br. s., 1H), 8.97 (dd, 1H), 8.61 (dd, 1H), 8.43 (s, 1H), 7.74 (dd, 1H), 7.42-7.49 (m, 3H), 7.27-7.33 (m, 2H)

Step 6: Preparation of N-(1-methyltetrazol-5-yl)-8-phenyl-7-(trifluoromethyl)-quinoline-6-carboxamide Oxalyl chloride (0.80 g, 6.3 mmol) was added to a stirred solution of 8-phenyl-7-(trifluoromethyl)quinoline-6-carboxylic acid (500 mg, 1.58 mmol) and DMAP (ca. 5 mg) in dichloromethane (25 mL) at 0° C. The reaction was warmed to room temperature and stirred for 2 hours, then left to stand over the weekend. The mixture was heated to reflux for 2 hours, and was then concentrated in vacuo under reduced pressure. The residue was dissolved in dichloromethane (50 mL) and 1-methyltetrazol-5-amine (156 mg, 1.58 mmol) was added in one portion. The reaction was stirred for 10 minutes at room temperature then triethylamine (0.64 g, 6.30 mmol) was added. After 2 hours the mixture was transferred to a microwave vial and heated at 100° C. for 2 hours. The reaction mixture was diluted with dichloromethane, sequentially washed with water then brine. The organics was passed through a phase separating cartridge and concentrated under reduced pressure. The residue was purified by flash chromatography (12 g silica), eluting with 0-5% methanol in dichloromethane, to give N-(1-methyltetrazol-5-yl)-8-phenyl-7-(trifluoromethyl)quinoline-6-carboxamide (191 mg, 30%).

1H NMR (400 MHz, CDCl$_3$) δ ppm 11.74 (br s, 1H), 9.05 (dd, 1H), 8.32-8.28 (m, 2H) 7.60-7.73 (m, 6H), 4.14 (s, 3H)

EXAMPLE P2. PREPARATION OF 7-METHOXY-N-(1-METHYLTETRAZOL-5-YL)-8-PHENYL-QUINOLINE-6-CARBOXAMIDE (COMPOUND 1.009)

Step 1: Preparation of dimethyl 2-[(2-benzyl-3-pyridyl)methylene]propanedioate A solution of dimethyl malonate (1.22 g, 9.20 mmol), 2-benzylpyridine-3-carbaldehyde (1.65 g, 8.37 mmol) and piperidine (0.1 mL) in methanol (20 mL) was stirred at room temperature overnight, and then heated under reflux for 8 hours. The cooled mixture was concentrated under reduced pressure, and the residue was dry-loaded onto celite and purified by flash chromatography (silica), eluting with ethyl acetate in iso-hexane, to give dimethyl 2-[(2-benzyl-3-pyridyl)methylene]-propanedioate (2.25 g, 86.4% Yield) as a colourless oil.

1H NMR (400 MHz, CDCl3) δ ppm 8.53 (dd, 1H), 7.95 (s, 1H) 7.61 (dd, 1H), 7.29-7.15 (m, 6H), 4.24 (s, 2H), 3.85 (s, 3H), 3.67 (s, 3H).

Step 2: Preparation of methyl 7-hydroxy-8-phenyl-quinoline-6-carboxylate

A oven dried microwave vial was charged with a solution of potassium tert-pentoxide in toluene (0.91 mL, 1.6 mmol, 1.7M), and then a solution of dimethyl 2-[(2-benzyl-3-pyridyl)methylene]propanedioate (0.44 g, 0.14 mmol) in dry tetrahydrofuran (5 mL) under nitrogen. The mixture was heated in a microwave oven at 100° C. for 30 min, then carefully acidified with 2M HCl, and concentrated to dryness under reduced pressure. The residue was dry loaded onto C18 silica and purified by reverse phase HPLC, eluting with 100% water to 100% acetonitrile, to give methyl 7-hydroxy-8-phenyl-quinoline-6-carboxylate (0.126 g, 32% Yield) as an off-white solid.

1H NMR (400 MHz, CDCl$_3$) δ ppm 10.91 (s, 1H) 8.91 (dd, 1H), 8.54 (s, 1H), 8.15 (dd, 1H) 7.55-7.41 (m, 5H), 7.27, (m, 1H), 4.07 (s, 3H)

Step 3: Preparation of methyl 7-methoxy-8-phenyl-quinoline-6-carboxylate

A solution of diazomethyl(trimethyl)silane in diethyl ether (0.67 mL, 1.35 mmol, 2.0 M) was added dropwise to a stirred suspension of methyl 7-hydroxy-8-phenyl-quinoline-6-carboxylate (188 mg, 0.67 mmol) in methanol (2 mL) at room temperature. The mixture was stirred overnight, when analysis showed that the reaction had not gone to completion. Toluene (ca. 5 mL) was added, followed by an additional solution of diazomethyl(trimethyl)silane in diethyl ether (0.67 mL, 1.35 mmol, 2.0 M). The solution was stirred overnight, quenched with acetic acid and concentrated under reduced pressure to leave methyl 7-methoxy-8-phenyl-quinoline-6-carboxylate (222 mg, 112% Yield) as a red solid.

1H NMR (400 MHz, CDCl$_3$) δ ppm 8.94 (dd, 1H), 8.32 (s, 1H), 8.20 (dd, 1H), 7.46-7.36 (m, 6H), 4.00 (s, 3H), 3.51 (s, 3H)

Step 4: Preparation of 7-methoxy-8-phenyl-quinoline-6-carboxylic acid

A solution of lithium hydroxide (34 mg, 1.43 mmol) in water (5 mL) was added to a solution of ethyl 7-methoxy-8-phenyl-quinoline-6-carboxylate (220 mg, 0.7159 mmol) in ethanol (5 mL), and the mixture was stirred at room temperature for 30 min. The ethanol was then removed in vacuo, ethyl acetate was added, and the mixture was acidified to pH7 and extracted 6 times with ethyl acetate. The aqueous layer was then lyophilised and triturated with hot ethyl acetate. The combined ethyl acetate layers were dried over magnesium sulfate, filtered and evaporated to dryness under reduced pressure to give 7-methoxy-8-phenyl-quinoline-6-carboxylic acid (167 mg, 84% Yield).

1H NMR (400 Mz CD3OD) δ ppm 8.69 (m, 1H), 8.35 (m, 2H), 7.49-7.33 (m, 6H), 3.41 (s, 3H)

Step 5: Preparation of 7-methoxy-N-(1-methyltetrazol-5-yl)-8-phenyl-quinoline-6-carboxamide To a suspension of 7-methoxy-8-phenyl-quinoline-6-carboxylic acid (167 mg, 0.60 mmol) in dichloromethane (5 mL), was added DMF (1 drop) and oxalyl chloride (0.21 mL, 2.4 mmol). The reaction was stirred for 5 minutes, when analysis showed complete consumption of the starting acid. The reaction mixture was concentrated to dryness under reduced pressure, and the residue was dissolved in dichloromethane (4 mL). 5-Amino-1-methyl-1H-tetrazole (129 mg, 1.290 mmol) and triethylamine (0.26 g, 2.58 mmol) were then added in one portion. The resultant mixture was heated in a microwave oven at 100° C. for 2 hours. The crude reaction mixture was then dry-loaded onto silica and purified by flash chromatography, eluting with methanol in dichloromethane (0-10%), to give 7-methoxy-N-(1-methyl-tetrazol-5-yl)-8-phenyl-quinoline-6-carboxamide (9 mg) as a pale brown solid.

1H NMR (400 MHz, CDCl3) δ ppm 10.75 (br. S, 1H), 9.00 (dd, 1H), 8.80 (s, 1H), 8.32 (dd, 1H), 7.57-7.46 (m, 6H), 4.14 (s, 3H), 3.59 (s, 3H).

EXAMPLE P3. PREPARATION OF 3-FLUORO-N-(1-METHYLTETRAZOL-5-YL)-8-PHENYL-7-(TRIFLUOROMETHYL)QUINOLINE-6-CARBOXAMIDE (COMPOUND 1.007)

Step 1: Preparation of 2-benzyl-5-fluoro-pyridine-3-carbaldehyde

A 20 ml microwave vial was charged with 2-chloro-5-fluoro-pyridine-3-carbaldehyde (1.00 g, 6.27 mmol), 2-benzyl-4,4,5,5-tetramethyl-1,3,2-dioxaborolane (1.1 equivalents, 6.89 mmol), [1,1'-Bis(diphenylphosphino)ferrocene] palladium(II) dichloride (PdCl$_2$(dppf); 0.1 equivalents, 0.63 mmol) and powdered sodium carbonate (3 equivalents, 18.80 mmol). A mixture of 1,4-dioxane (9 mL) and water (5 mL) were added, the mixture was flushed with nitrogen, and then heated by microwave at 90° C. for three periods of 2 hours. The cooled mixture was then adsorbed directly onto silica and purified through a 40 g silica-gel column, eluting with isohexane:ethyl acetate (100:0% to 70:30%) to afford 2-benzyl-5-fluoro-pyridine-3-carbaldehyde (460 mg) as a colourless oil.

1H NMR (400 MHz, CDCl3) δ ppm 10.35 (s, 1H), 8.64 (d, 1H), 7.84 M, 1H), 7.31-7.25 (m, 3H). 7.23-7.14 (m, 2H),

Step 2: Preparation of ethyl 3-fluoro-8-phenyl-7-(trifluoromethyl)quinoline-6-carboxylate Using the method described in Preparative Example 1, Step 4, 2-benzyl-5-fluoro-pyridine-3-carbaldehyde was converted to ethyl 3-fluoro-8-phenyl-7-(trifluoro-methyl)quinoline-6-carboxylate.

1H NMR (400 MHz, CDCl3) δ ppm 8.89 (d, 1H), 8.09 (s, 1H), 7.86 (m, 1H), 7.50-7.43 (m, 3H), 7.36-7.29 (m, 2H), 4.44 (q, 2H), 1.41 (t, 3H)

Step 3: Preparation of 3-fluoro-8-phenyl-7-(trifluoromethyl)quinoline-6-carboxylic acid Using the method described in Preparative Example 2, Step 4, 3-fluoro-8-phenyl-7-(trifluoromethyl)quinoline-6-carboxylate was converted to 3-fluoro-8-phenyl-7-(trifluoromethyl)quinoline-6-carboxylic acid.

m/z 336.3 (M+H)

Step 4: Preparation of 3-fluoro-N-(1-methyltetrazol-5-yl)-8-phenyl-7-(trifluoro-methyl)quinoline-6-carboxamide Using the method described in Preparative Example 2, Step 5, 3-fluoro-8-phenyl-7-(trifluoromethyl)quinoline-6-carboxylic acid was converted to 3-fluoro-N-(1-methyltetrazol-5-yl)-8-phenyl-7-(trifluoromethyl)quinoline-6-carboxamide.

1H NMR (400 MHz, CD3CN) δ ppm 9.70 (br s, 1H), 8.90 (d, 1H), 8.39 (br, 1H), 8.20 (m, 1H), 7.55-7.49 (m, 3H), 7.40-7.34 (m, 2H), 4.03 (s, 3H)

EXAMPLE P4: PREPARATION OF 7-METHYL-8-(4-METHYLSULFANYLPHENYL)-N-(1-METHYLTETRAZOL-5-YL)QUINOLINE-6-CARBOXAMIDE (COMPOUND 1.030)

Step 1: Preparation of methyl 4-amino-3-bromo-2-methyl-benzoate

A stirred solution of methyl 4-amino-2-methyl-benzoate (500 mg, 3.03 mmol) in dimethylformamide (10 mL) was cooled in an ice-bath to 5° C., and N-bromosuccinimide (540 mg, 3.03 mmol) was added portion wise over 5 mins whilst maintaining the temperature between 5° C. and 7° C. The clear pale yellow reaction mixture was stirred in the ice-bath for a further 30 mins, and then poured into water. A dense white precipitate formed, which was extracted into diethyl ether. The ether extracts were separated, washed with water, dried over anhydrous magnesium sulphate, and the solvent was evaporated under reduced pressure to yield an inseparable 60:40 mixture of methyl 4-amino-3-bromo-2-methyl-benzoate and methyl 4-amino-5-bromo-2-methyl-benzoate, which was used directly in the next step.

1H NMR (400 MHz, CDCl3) δ ppm inter alia 7.71 (d, 1H), 6.60 (d, 1H), 4.52 (br s, 2H), 3.84 (s, 3H), 2.71 (s, 3H)

Step 2: Preparation of methyl 8-bromo-7-methyl-quinoline-6-carboxylate

A stirred suspension of a 60:40 mixture of methyl 4-amino-3-bromo-2-methyl-benzoate and methyl 4-amino-5-bromo-2-methyl-benzoate (200 mg, 0.82 mmol) in n-butanol (5 mL, 55 mmol) was treated with conc. hydrochloric acid (0.2 mL) and p-chloranil (200 mg, 0.81 mmol). The resulting slurry was then heated to 100° C. and prop-2-enal (acrolein) (0.1 mL, 1 mmol) was added dropwise. Heating was continued for a further 30 mins, then the mixture was cooled and partitioned between water and dichloromethane. The dichloromethane layer was adsorbed on to silica-gel by evaporation under reduced pressure, and separated by flash chromatography (silica, eluting with an ethyl acetate/isohexane gradient) to afford an inseparable 60:40 mixture of methyl 8-bromo-7-methyl-quinoline-6-carboxylate and methyl 8-bromo-5-methyl-quinoline-6-carboxylate (155 mg) as a tan solid.

1H NMR (400 MHz, CDCl3) δ ppm inter alia 9.11 (td, 1H), 8.28 (s, 1H), 8.20 (dd, 1H), 7.49 (dd, 1H), 3.99 (s, 3H), 2.90 (s, 3H)

Step 3: Preparation of methyl 8-(4-methylsulfanyl-phenyl)-7-methyl-quinoline-6-carboxylate A stirred solution of a 60:40 mixture of methyl 8-bromo-7-methyl-quinoline-6-carboxylate and methyl 8-bromo-5-methyl-quinoline-6-carboxylate (310 mg, 1.14 mmol) in t-butanol (10.0 mL) was treated with potassium phosphate (610 mg, 2.79 mmol), 2-dicyclohexylphosphino-2',6'-dimethoxybiphenyl (S-Phos: 90 mg, 0.069 mmol), tris(dibenzylideneacetone)dipalladium(O) (50 mg, 0.053 mmol) and 4-methylsulfanylphenyl boronic acid (270 mg, 1.61 mmol) in a 20 ml microwave vial, blanketed with nitrogen. The vial was capped and the reaction mixture was heated by microwave to 100° C. for 45 mins. The cooled mixture was filtered through hyflo and washed with dichloromethane to yield a yellow filtrate, which was adsorbed on to silica-gel and purified by flash chromatography (silica, eluting with an ethyl acetate/isohexane gradient) to afford methyl 8-(4-methylsulfanylphenyl)-7-methyl-quinoline-6-carboxylate (190 mg) as a tan solid.

1H NMR (400 MHz, CDCl3) δ ppm 8.92 (dd, 1H), 8.35 (s, 1H), 8.20 (dd, 1H), 7.44-7.35 (m, 3H), 7.24-7.16 (m, 2H), 3.99 (s, 3H), 2.56 (s, 3H), 2.45 (s, 3H)

Step 4: Preparation of 7-methyl-8-(4-methylsulfanylphenyl)quinoline-6-carboxylic acid Using the method described in Preparative Example 2, Step 4, but using ethanol in place of methanol, methyl 8-(4-methylsulfanylphenyl)-7-methyl-quinoline-6-carboxylate was converted to 7-methyl-8-(4-methylsulfanylphenyl)quinoline-6-carboxylic acid.

1H NMR (400 MHz, CDCl3/CD3OD) δ ppm 8.74 (dd, 1H), 8.17 (dd, 1H), 7.91 (s, 1H), 7.39 (d, 2H), 7.34-7.28 (m, 1H), 7.20 (d, 2H), 2.56 (s, 3H), 2.37 (s, 3H)

Step 5: Preparation of 7-methyl-8-(4-methylsulfanylphenyl)-N-(1-methyltetrazol-5-yl)quinoline-6-carboxamide A stirred suspension of 7-methyl-8-(4-methylsulfanylphenyl)quinoline-6-carboxylic acid (0.59 mmol) in acetonitrile (5 mL) was treated with N,N'-carbonyldiimidazole (CDI: 140 mg, 0.86 mmol) in a single portion. The resultant suspension was heated to 90° C. for 4 hours, adding three further portions of CDI (3×140 mg) during this time. The reaction mixture was then cooled, filtered through hyflo, and evaporated under reduced pressure to afford the crude acyl imidazole. This was dissolved in 2-methyl tetrahydrofuran (10 mL) and treated with 5-amino-1-methyltetrazole (100 mg, 1.01 mmol) and 1,8-diazabicyclo[5,4,0]-7-undecene (DBU) (0.25 mL, 1.7 mmol). The stirred mixture was heated to 90° C. for 3 hours, adding a further portion of 5-amino-1-methyltetrazole (100 mg, 1.01 mmol) after 1 hour. The mixture was then cooled and the solvent was evaporated under reduced pressure. The residue was partitioned between dichloromethane and water, and the dichloromethane layer was washed with water and brine before being dried by passing through a phase-separating cartridge. The filtrate was adsorbed on to silica-gel and separated by chromatography (Silica, eluting with an methanol/dichloromethane gradient) to afford the crude product as a yellow solid. Trituration with diethyl ether afforded 7-methyl-8-(4-methylsulfanylphenyl)-N-(1-methyltetrazol-5-yl)quinoline-6-carboxamide (35 mg) as a cream solid.

1H NMR (400 MHz, CD3OD) δ ppm 8.92-8.82 (m, 1H), 8.29 (d, 1H), 8.18 (s, 1H), 7.47 (dd, 1H), 7.42 (d, 2H), 7.22 (d, 2H), 4.14 (s, 3H), 2.58 (s, 3H), 2.41 (s, 3H)

EXAMPLE P5: PREPARATION OF 7-METHYL-8-(4-METHYLSULFONYLPHENYL)-N-(1-METHYLTETRAZOL-5-YL)QUINOLINE-6-CARBOXAMIDE (COMPOUND 1.031)

A stirred solution of 7-methyl-8-(4-methylsulfanylphenyl)-N-(1-methyltetrazol-5-yl)quinoline-6-carboxamide (25 mg, 0.064 mmol) in dichloromethane (2 mL) and methanol (2 mL) was treated dropwise with peracetic acid (0.15 mL) at room temperature. The mixture was stirred for 1 hour, then carefully evaporated to dryness under reduced pressure to afford 7-methyl-8-(4-methylsulfonylphenyl)-N-(1-methyltetrazol-5-yl)quinoline-6-carboxamide (27 mg) as a cream solid.

1H NMR (400 MHz, CD3OD) δ ppm 8.96 (d, 1H), 8.73 (d, 1H), 8.42 (s, 1H), 8.17 (d, 2H), 7.76 (dd, 1H), 7.59 (d2H), 4.15 (s, 3H), 3.24 (s, 3H), 2.43 (s, 3H)

EXAMPLE P6: PREPARATION OF 7-CHLORO-N-(1-METHYLTETRAZOL-5-YL)-8-PHENYL-QUINOLINE-6-CARBOXAMIDE (COMPOUND 1.011)

Step 1: Preparation of methyl 7-chloro-8-phenyl-quinoline-6-carboxylate and 7-chloro-8-phenyl-quinoline-6-carboxylic acid A stirred suspension of methyl 7-hydroxy-8-phenyl-quinoline-6-carboxylate (2.0 g, 7.16 mmol) in phosphorus oxychloride (10 mL) was heated by microwave to 120° C. for 8 hours, then to 200° C. for 7 mins. The cooled mixture was added dropwise to aqueous sodium bicarbonate solution, and extracted with ethyl acetate. The ethyl acetate extract was extracted with aqueous sodium bicarbonate, dried and evaporated under reduced pressure to afford crude methyl 7-chloro-8-phenyl-quinoline-6-carboxylate, which was purified by flash chromatography (Silica, eluting with an ethyl acetate/isohexane gradient) to afford the pure compound (212 mg).

1H NMR (400 MHz, CDCl3) δ ppm 8.96 (d, 1H), 8.27 (s, 1H), 8.21 (m, 1H), 7.58-7.40 (m, 4H), 7.32 (m, 2H), 4.01 (s, 3H)

The bicarbonate extracts were combined with the original bicarbonate reaction quench and carefully acidified using c. hydrochloric acid, and this was extracted with ethyl acetate (3×). These combined ethyl acetate extracts were dried and the solvent was removed under reduced pressure to afford 7-chloro-8-phenyl-quinoline-6-carboxylic acid (626 mg).

1H NMR (400 MHz, CD3OD) δ ppm 8.92 (m, 1H), 8.45 (m, 1H), 8.38 (s, 1H), 7.60-7.38 (m, 4H), 7.29 (m, 2H)

Step 2: Preparation of 7-chloro-N-(1-methyltetrazol-5-yl)-8-phenyl-quinoline-6-carboxamide A stirred solution of 7-chloro-8-phenyl-quinoline-6-carboxylic acid (168 mg, 0.44 mmol) and 5-amino-1-methyltetrazole (1.2 equivalents, 0.53 mmol) in dichloromethane (3 mL) was treated with 4-(dimethylamino) pyridine (DMAP: 3 equivalents, 1.33 mmol), and the reaction mixture was stirred for 1 hour. 1-propanephosphonic acid cyclic anhydride (PPAA: (50 mass % in ethyl acetate); 6 equivalents, 2.66 mmol) was added, and the reaction mixture was transferred to a microwave vial and heated 120° C. for 10 mins. The mixture was cooled and the solvent was removed under reduced pressure. The residue was dissolved in ethyl acetate, which was washed with water (3×), brine, dried over magnesium sulphate, and the solvent was removed under reduced pressure. The residue was adsorbed on to silica-gel and purified by flash chromatography (Silica, eluting with a methanol/dichloromethane gradient) to afford 7-chloro-N-(1-methyltetrazol-5-yl)-8-phenyl-quinoline-6-carboxamide (42 mg).

1H NMR (400 MHz, CD3CN) δ ppm 9.61 (br s, 1H), 8.91 (d, 1H), 8.45 (dd, 1H), 8.32 (s, 1H), 7.63-7.45 (m, 4H), 7.39 (m, 2H), 4.05 (s, 3H).

EXAMPLE P7: PREPARATION OF 7-METHYLSULFANYL-N-(1-METHYLTETRAZOL-5-YL)-8-PHENYL-QUINOLINE-6-CARBOXAMIDE (COMPOUND 1.032)

Step 1: Preparation of 7-methylsulfanyl-8-phenyl-quinoline-6-carboxylic acid

A stirred solution of methyl 7-chloro-8-phenyl-quinoline-6-carboxylate (130 mg, 0.437 mmol) was dissolved in dimethylformamide (3 mL) and sodium thiomethoxide (2 equivalents, 0.874 mmol) was added. The mixture was stirred at room temperature for 1 hour, then heated by microwave to 100° C. for 35 mins. A further 2 equivalents of sodium thiomethoxide was added and the mixture was heated by microwave at 140° C. for 1 hour. A further 2 equivalents of sodium thiomethoxide was added and the mixture was heated by microwave at 140° C. for a further 2 hours, followed by heating to 160° C. for 30 mins. The cooled reaction mixture was diluted with water and washed with ether (2×). The aqueous layer was then acidified, and extracted with diethyl ether (6×). The combined ether extracts were dried over magnesium sulphate, then concentrated under reduced pressure to afford very crude 7-methylsulfanyl-8-phenyl-quinoline-6-carboxylic acid, which was used in the next step without further purification.

m/z 296.1 (M+H)

Step 2: Preparation of 7-methylsulfanyl-N-(1-methyltetrazol-5-yl)-8-phenyl-quinoline-6-carboxamide Using the method described in Preparative Example 6, Step 2, 7-methylsulfanyl-8-phenyl-quinoline-6-carboxylic acid was converted to 7-methylsulfanyl-N-(1-methyltetrazol-5-yl)-8-phenyl-quinoline-6-carboxamide.

1H NMR (400 MHz, CD3CN) δ ppm 9.70 (br s, 1H), 8.88 (m, 1H), 8.39 (m, 1H), 8.21 (s, 1H), 7.60-7.42 (m, 4H), 7.40-7.35 (m, 2H), 4.10 (s, 3H), 2.13 (s, 3H)

EXAMPLE P8: PREPARATION OF 7-METHYL-SULFONYL-N-(1-METHYLTETRAZOL-5-YL)-8-PHENYL-QUINOLINE-6-CARBOXAMIDE (COMPOUND 1.010)

A stirred solution of 7-methylsulfanyl-N-(1-methyltetrazol-5-yl)-8-phenyl-quinoline-6-carboxamide (147 mg, 0.39 mmol) in acetic acid (10 mL) was treated with a catalytic amount of sodium tungstate dihydrate (100 mass %) followed by the dropwise addition of hydrogen peroxide (1 mL). The mixture was heated to 65° C., and a further 3 mL of hydrogen peroxide was added in 1 mL amounts. The mixture was cooled and quenched with sodium metabisulfite. This was extracted with ethyl acetate, and the extracts were dried over magnesium sulphate, then adsorbed onto silica-gel under reduced pressure. Separation by flash chromatography (Silica (20-40 micron), eluting with a methanol/dichloromethane gradient) afforded 7-methylsulfonyl-N-(1-methyltetrazol-5-yl)-8-phenyl-quinoline-6-carboxamide (29 mg).

1H NMR (400 MHz, CDCl3) δ ppm 10.30 (br s, 1H), 9.08 (m, 1H), 8.88-8.78 (m, 2H), 7.67-7.48 (m, 4H), 7.45-7.38 (m, 2H), 4.25 (s, 3H), 3.06 (s, 3H).

TABLE 1

Examples of herbicidal compounds of the present invention.

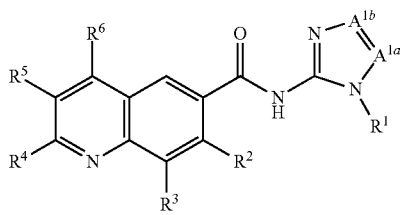

| Compound | $A^{1a}$ | $A^{1b}$ | $R^1$ | $R^2$ | $R^3$ | $R^4$ | $R^5$ | $R^6$ | NMR |
|---|---|---|---|---|---|---|---|---|---|
| 1.001 | N | N | Me | $CF_3$ | phenyl | H | H | H | 1H NMR (400 MHz, CDCl$_3$) δ ppm 11.74 (br s, 1H), 9.05 (dd, 1H), 8.32-8.28 (m, 2H) 7.60-7.73 (m, 6H), 4.14 (s, 3H) |
| 1.002 | N | N | Et | $CF_3$ | phenyl | H | H | H | 1H NMR (400 MHz, CDCl$_3$) δ ppm 11.50 (br s, 1H), 9.04 (m, 1H), 8.31-8.24 (m, 2H), 7.55 (m, 1H), 7.53-7.42 (m, 3H0, 7.40 (m, 2H), 4.49 (q, 2H), 1.61 (t, 3H) |
| 1.003 | N | N | nPr | $CF_3$ | phenyl | H | H | H | m/z = 427.2 (M + H) |
| 1.004 | N | N | Me | $CF_3$ | phenyl | Me | H | H | |
| 1.005 | N | N | Me | $CF_3$ | phenyl | $CF_3$ | H | H | |
| 1.006 | N | N | Me | $CF_3$ | phenyl | Me | F | H | |
| 1.007 | N | N | Me | $CF_3$ | phenyl | H | F | H | 1H NMR (400 MHz, CD3CN) δ ppm 9.70 (br s, 1H), 8.90 (d, 1H), 8.39 (br, 1H), 8.20 (m, 1H), 7.55-7.49 (m, 3H), 7.40-7.34 (m, 2H), 4.03 (s, 3H) |
| 1.008 | N | N | Me | Me | phenyl | H | H | H | |
| 1.009 | N | N | Me | MeO— | phenyl | H | H | H | 1H NMR (400 MHz, CDCl3) δ ppm 10.75 (br. S, 1H), 9.00 (dd, 1H), 8.80 (s, 1H), 8.32 (dd, 1H), 7.57-7.46 (m, |

TABLE 1-continued

Examples of herbicidal compounds of the present invention.

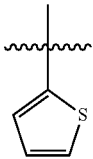

| Compound | $A^{1a}$ | $A^{1b}$ | $R^1$ | $R^2$ | $R^3$ | $R^4$ | $R^5$ | $R^6$ | NMR |
|---|---|---|---|---|---|---|---|---|---|
| | | | | | | | | | 6H), 4.14 (s, 3H), 3.59 (s, 3H). |
| 1.010 | N | N | Me | —S(O)$_2$Me | phenyl | H | H | H | 1H NMR (400 MHz, CDCl3) δ ppm 10.30 (br s, 1H), 9.08 (m, 1H), 8.88-8.78 (m, 2H), 7.67-7.48 (m, 4H), 7.45-7.38 (m, 2H), 4.25 (s, 3H), 3.06 (s, 3H) |
| 1.011 | N | N | Me | Cl | phenyl | H | H | H | 1H NMR (400 MHz, CD3CN) δ ppm 9.61 (br s, 1H), 8.91 (d, 1H), 8.45 (dd, 1H), 8.32 (s, 1H), 7.63-7.45 (m, 4H), 7.39 (m, 2H), 4.05 (s, 3H). |
| 1.012 | N | N | Me | CF$_3$ | phenyl | H | H | Cl | |
| 1.013 | CH | N | Me | CF$_3$ | phenyl | H | H | H | |
| 1.014 | N | CH | Me | CF$_3$ | phenyl | H | H | H | |
| 1.015 | N | N | Me | CF$_3$ | 4-Cl-phenyl- | H | H | H | |
| 1.016 | N | N | Me | CF$_3$ | 4-MeO-phenyl- | H | H | H | |
| 1.017 | N | N | Me | CF$_3$ | 4-Me-phenyl- | H | H | H | 1H NMR (400 MHz, CD3CN) δ ppm 9.78 (br s, 1H), 8.94 (m, 1H), 8.45 (m, 1H), 8.37 (br, 1H), 7.66 (m, 1H), 7.31 (d, 2H), 7.25 (d, 2H), 4.04 (s, 3H), 2.44 (s, 3H) |
| 1.018 | N | N | Me | CF$_3$ | 4-CF$_3$-phenyl | H | H | H | |
| 1.019 | N | N | Me | CF$_3$ | 4-NO$_2$-phenyl- | H | H | H | |
| 1.020 | N | N | Me | CF$_3$ | 4-MeS(O)$_2$-phenyl- | H | H | H | |
| 1.021 | N | N | Me | CF$_3$ | 4-CN-phenyl- | H | H | H | |
| 1.022 | N | N | Me | CF$_3$ | 4-CF$_3$O-phenyl | H | H | H | |
| 1.023 | N | N | Me | CF$_3$ | 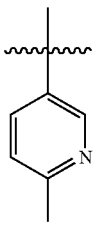 | H | H | H | |
| 1.024 | N | N | Me | CF$_3$ | 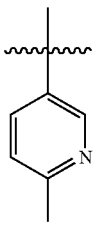 | H | H | H | |

TABLE 1-continued

Examples of herbicidal compounds of the present invention.

| Compound | $A^{1a}$ | $A^{1b}$ | $R^1$ | $R^2$ | $R^3$ | $R^4$ | $R^5$ | $R^6$ | NMR |
|---|---|---|---|---|---|---|---|---|---|
| 1.025 | N | N | Me | $CF_3$ | 3-Me-phenyl- | H | H | H | |
| 1.026 | N | N | Me | $CF_3$ | 3,4-diMe-phenyl- | H | H | H | |
| 1.027 | N | N | Me | $CF_3$ | 3-Cl-phenyl- | H | H | H | |
| 1.028 | N | N | Me | $CF_3$ | 3-MeO-phenyl- | H | H | H | |
| 1.029 | N | N | Me | $CF_3$ | 2F-phenyl- | H | H | H | |
| 1.030 | N | N | Me | Me | 4-MeS-phenyl- | H | H | H | 1H NMR (400 MHz, CD3OD) δ ppm 8.92-8.82 (m, 1H), 8.29 (d, 1H), 8.18 (s, 1H), 7.47 (dd, 1H), 7.42 (d, 2H), 7.22 (d, 2H), 4.14 (s, 3H), 2.58 (s, 3H), 2.41 (s, 3H) |
| 1.031 | N | N | Me | Me | 4-MeS(O)$_2$-phenyl- | H | H | H | 1H NMR (400 MHz, CD3OD) δ ppm 8.96 (d, 1H), 8.73 (d, 1H), 8.42 (s, 1H), 8.17 (d, 2H), 7.76 (dd, 1H), 7.59 (d2H), 4.15 (s, 3H), 3.24 (s, 3H), 2.43 (s, 3H) |
| 1.032 | N | N | Me | MeS— | phenyl | H | H | H | 1H NMR (400 MHz, CD3CN) δ ppm 9.70 (br s, 1H), 8.88 (m, 1H), 8.39 (m, 1H), 8.21 (s, 1H), 7.60-7.42 (m, 4H), 7.40-7.35 (m, 2H), 4.10 (s, 3H), 2.13 (s, 3H) |
| 1.033 | N | N | phenyl | $CF_3$ | phenyl | H | H | H | 1H NMR (400 MHz, CDCl3) δ ppm 11.01 (br s, 1H), 8.94 (m, 1H), 8.27-8.05 (m, 2H), 7.62-7.35 (m, 9H), 7.30-7.20 (m, 2H) |
| 1.034 | N | N | Me | Me | 4-MeO-phenyl- | H | H | H | 1H NMR (400 MHz, CDCl3) δ ppm 8.91 (dd, 1H), 8.26 (dd, 1H), 8.15 (s, 1H), 7.44 (dd, 1H), 7.25-7.18 (m, 2H), 7.12-7.04 (m, 2H), 4.14 (s, 3H), 3.91 (s, 3H), 2.42 (s, 3H) |
| 1.035 | N | N | Me | Me | 4-F-phenyl- | H | H | H | 1H NMR (400 MHz, CDCl3) δ ppm 8.91 (dd, 1H), 8.27 (dd, 1H), 8.19 (s, 1H), 7.46 (dd, 1H), 7.29-7.18 (m, 4H), 4.15 (s, 3H), 2.40 (s, 3H) |
| 1.036 | N | N | Me | Me | 4-Cl-phenyl- | H | H | H | 1H NMR (400 MHz, CDCl3) δ ppm 11.24 (br. s., 1H), 8.95 (dd, 1H), 8.47 (s, 1H), 8.35 (dd1H), 7.52-7.47 (m, 2H), 7.45 (dd, 1H), 7.26- |

TABLE 1-continued

Examples of herbicidal compounds of the present invention.

| Compound | $A^{1a}$ | $A^{1b}$ | $R^1$ | $R^2$ | $R^3$ | $R^4$ | $R^5$ | $R^6$ | NMR |
|---|---|---|---|---|---|---|---|---|---|
| 1.037 | N | N | Me | Me | 4-MeO-phenyl- | Me | H | H | 7.22 (m, 2H), 4.16 (s, 3H), 2.43 (s, 3H) 1H NMR (400 MHz, CDCl3) δ ppm 11.99 (br.s, 1H), 8.74 (d, 1H), 8.53 (s, 1H), 7.56 (d, 1H), 7.12 (d, 2H), 6.99 (d, 2H), 4.10 (s, 3H), 3.84 (s, 3H), 2.86 (s, 3H), 2.27 (s, 3H) |
| 1.038 | N | N | Me | Me | 4-MeS(O)$_2$-phenyl- | Me | H | H | 1H NMR (400 MHz, CD3OD) δ ppm 8.21 (s, 1H), 8.20 (d1H), 8.08 (d2H), 7.55 (d, 2H), 7.38 (d, 1H), 4.14 (s, 3H), 3.23 (s, 3H), 2.60 (s, 3H), 2.39 (s, 3H) |
| 1.039 | N | N | Me | Me | 2-thienyl | H | H | H | 1H NMR (400 MHz, CD3OD) δ ppm 8.92 (dd, 1H), 8.26 (dd, 1H), 8.15 (s, 1H), 7.53 (dd1H), 7.46 (dd, 1H), 7.27 (dd, 1H), 7.12 (dd, 1H), 4.14 (s, 3H), 2.47 (s, 3H) |
| 1.040 | N | N | Me | Me | 3-pyridyl | H | H | H | 1H NMR (400 MHz, CD3OD) δ ppm 8.84 (dd, 1H), 8.65 (dd, 1H), 8.49 (dd, 1H), 8.42 (dd, 1H), 8.33 (s, 1H), 7.80 (td, 1H), 7.61 (ddd, 1H), 7.56 (dd, 1H), 4.14 (s, 3H), 2.44 (s, 3H) |
| 1.041 | N | N | Me | Me | 5-pyrimidinyl | H | H | H | 1H NMR (400 MHz, CD3OD) δ ppm 9.28 (s, 1H), 8.88 (dd, 1H), 8.78 (s, 2H), 8.38 (dd, 1H), 8.33 (s, 1H), 7.56 (dd, 1H), 4.15 (s, 3H), 2.52 (s, 3H) |
| 1.042 | N | N | Me | Me | 1-methylpyrazol-4-yl | H | H | H | 1H NMR (400 MHz, d6-DMSO) δ ppm 11.76 (s, 1H), 8.94 (br d, 1H), 8.45 (d, 1H), 8.27 (s, 1H), 7.90 (s, 1H), 7.58 (m, 2H), 4.05 (s, 3H), 3.96 (s, 3H), 2.50 (s, 3H) |

TABLE 1-continued

Examples of herbicidal compounds of the present invention.

| Compound | $A^{1a}$ | $A^{1b}$ | $R^1$ | $R^2$ | $R^3$ | $R^4$ | $R^5$ | $R^6$ | NMR |
|---|---|---|---|---|---|---|---|---|---|
| 1.043 | N | N | Me | Me | 3,5-dimethylisoxazol-4-yl | H | H | H | 1H NMR (400 MHz, d6-DMSO) δ ppm 11.83 (s, 1H), 8.94 (dd, 1H), 8.52 (dd, 1H), 8.45 (s, 1H), 7.63 (dd, 1H), 4.06 (s, 3H), 2.39 (s, 3H), 2.15 (s, 3H), 1.92 (s, 3H) |
| 1.044 | N | N | Me | Me | furan-3-yl | H | H | H | 1H NMR (400 MHz, d6-DMSO) δ ppm 11.78 (s, 1H), 8.94 (dd, 1H), 8.47 (dd, 1H), 8.34 (s, 1H), 7.84 (t, 1H), 7.81 (m, 1H), 7.59 (dd, 1H), 6.66 (dd, 1H), 4.05 (s, 3H), 2.49 (s, 3H) |
| 1.045 | N | N | Me | —S(O)Me | phenyl | H | H | H | |
| 1.046 | N | N | Me | Cl | 4-MeS(O)$_2$-phenyl- | H | H | H | |
| 1.047 | N | N | Et | CF$_3$ | 4-MeS(O)$_2$-phenyl- | H | H | H | |
| 1.048 | N | N | Et | Cl | 4-MeS(O)$_2$-phenyl- | H | H | H | |
| 1.049 | N | N | Me | CF$_3$ | pyrazol-1-yl | H | H | H | 1H NMR (400 MHz, CD3CN) δ ppm 9.05 (dd, 1H), 8.59-8.47 (m, 2H), 7.95 (d, 1H), 7.82 (d, 1H), 7.79 (dd, 1H), 6.61 (dd, 1H), 4.04 (s, 3H) |
| 1.050 | N | N | Me | CF$_3$ | imidazol-1-yl | H | H | H | |
| 1.051 | N | N | Me | CF$_3$ | 1,2,4-triazol-1-yl | H | H | H | |
| 1.052 | N | N | Et | CF$_3$ | pyrazol-1-yl | H | H | H | |

TABLE 2

Examples of herbicidal compounds of the present invention.

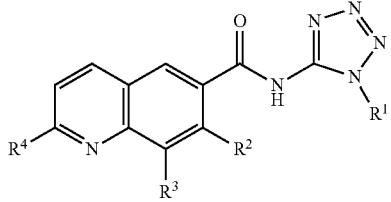

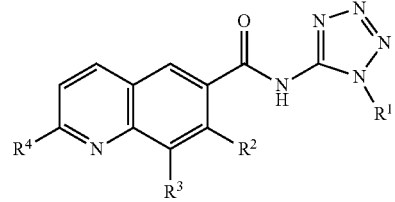

| Compound | R¹ | R² | R³ | R⁴ |
|---|---|---|---|---|
| 2.001 | Et | CF₃ | 4-Cl-phenyl | H |
| 2.002 | n-Pr | CF₃ | 4-Cl-phenyl | H |
| 2.003 | Et | CF₃ | 4-F-phenyl | H |
| 2.004 | Me | CF₃ | 4-F-phenyl | H |
| 2.005 | n-Pr | CF₃ | 4-F-phenyl | H |
| 2.006 | n-Pr | CF₃ | 4-MeS(O)₂-phenyl | H |
| 2.007 | Et | CF₃ | 4-MeS-phenyl | H |
| 2.008 | Me | CF₃ | 4-MeS-phenyl | H |
| 2.009 | n-Pr | CF₃ | 4-MeS-phenyl | H |
| 2.010 | Et | CF₃ | 4-Me-phenyl | H |
| 2.011 | n-Pr | CF₃ | 4-Me-phenyl | H |
| 2.012 | n-Pr | CF₃ | pyrazol-1-yl | H |
| 2.013 | Et | CF₃ | furan-3-yl | H |
| 2.014 | Me | CF₃ | furan-3-yl | H |
| 2.015 | n-Pr | CF₃ | furan-3-yl | H |
| 2.016 | Et | CF₃ | 3,5-dimethyl-isoxazol-4-yl | H |
| 2.017 | Me | CF₃ | 3,5-dimethyl-isoxazol-4-yl | H |
| 2.018 | n-Pr | CF₃ | 3,5-dimethyl-isoxazol-4-yl | H |
| 2.019 | Et | CF₃ | thien-2-yl | H |
| 2.020 | n-Pr | CF₃ | thien-2-yl | H |
| 2.021 | Et | CF₃ | 1-methyl-pyrazol-4-yl | H |
| 2.022 | Me | CF₃ | 1-methyl-pyrazol-4-yl | H |
| 2.023 | n-Pr | CF₃ | 1-methyl-pyrazol-4-yl | H |
| 2.024 | Et | CF₃ | pyrimidin-5-yl | H |
| 2.025 | Me | CF₃ | pyrimidin-5-yl | H |
| 2.026 | n-Pr | CF₃ | pyrimidin-5-yl | H |
| 2.027 | Et | CF₃ | pyridin-3-yl | H |
| 2.028 | Me | CF₃ | pyridin-3-yl | H |
| 2.029 | n-Pr | CF₃ | pyridin-3-yl | H |
| 2.030 | Et | Cl | phenyl | H |
| 2.031 | n-Pr | Cl | phenyl | H |
| 2.032 | Et | Cl | 4-Cl-phenyl | H |
| 2.033 | Me | Cl | 4-Cl-phenyl | H |
| 2.034 | n-Pr | Cl | 4-Cl-phenyl | H |
| 2.035 | Et | Cl | 4-F-phenyl | H |
| 2.036 | Me | Cl | 4-F-phenyl | H |
| 2.037 | n-Pr | Cl | 4-F-phenyl | H |
| 2.038 | n-Pr | Cl | 4-MeS(O)₂-phenyl | H |
| 2.039 | Et | Cl | 4-MeS-phenyl | H |
| 2.040 | Me | Cl | 4-MeS-phenyl | H |
| 2.041 | n-Pr | Cl | 4-MeS-phenyl | H |
| 2.042 | Et | Cl | 4-Me-phenyl | H |
| 2.043 | Me | Cl | 4-Me-phenyl | H |
| 2.044 | n-Pr | Cl | 4-Me-phenyl | H |
| 2.045 | Et | Cl | pyrazol-1-yl | H |
| 2.046 | Me | Cl | pyrazol-1-yl | H |
| 2.047 | n-Pr | Cl | pyrazol-1-yl | H |
| 2.048 | Et | Cl | furan-3-yl | H |
| 2.049 | Me | Cl | furan-3-yl | H |
| 2.050 | n-Pr | Cl | furan-3-yl | H |
| 2.051 | Et | Cl | 3,5-dimethyl-isoxazol-4-yl | H |
| 2.052 | Me | Cl | 3,5-dimethyl-isoxazol-4-yl | H |
| 2.053 | n-Pr | Cl | 3,5-dimethyl-isoxazol-4-yl | H |
| 2.054 | Et | Cl | thien-2-yl | H |
| 2.055 | Me | Cl | thien-2-yl | H |
| 2.056 | n-Pr | Cl | thien-2-yl | H |
| 2.057 | Et | Cl | 1-methyl-pyrazol-4-yl | H |
| 2.058 | Me | Cl | 1-methyl-pyrazol-4-yl | H |
| 2.059 | n-Pr | Cl | 1-methyl-pyrazol-4-yl | H |
| 2.060 | Et | Cl | pyrimidin-5-yl | H |
| 2.061 | Me | Cl | pyrimidin-5-yl | H |
| 2.062 | n-Pr | Cl | pyrimidin-5-yl | H |
| 2.063 | Et | Cl | pyridin-3-yl | H |
| 2.064 | Me | Cl | pyridin-3-yl | H |
| 2.065 | n-Pr | Cl | pyridin-3-yl | H |
| 2.066 | Et | —SMe | phenyl | H |
| 2.067 | n-Pr | —SMe | phenyl | H |
| 2.068 | Et | —SMe | 4-Cl-phenyl | H |
| 2.069 | Me | —SMe | 4-Cl-phenyl | H |
| 2.070 | n-Pr | —SMe | 4-Cl-phenyl | H |
| 2.071 | Et | —SMe | 4-F-phenyl | H |
| 2.072 | Me | —SMe | 4-F-phenyl | H |
| 2.073 | n-Pr | —SMe | 4-F-phenyl | H |
| 2.074 | Et | —SMe | 4-MeS(O)₂-phenyl | H |
| 2.075 | Me | —SMe | 4-MeS(O)₂-phenyl | H |
| 2.076 | n-Pr | —SMe | 4-MeS(O)₂-phenyl | H |
| 2.077 | Et | —SMe | 4-MeS-phenyl | H |
| 2.078 | Me | —SMe | 4-MeS-phenyl | H |
| 2.079 | n-Pr | —SMe | 4-MeS-phenyl | H |
| 2.080 | Et | —SMe | 4-Me-phenyl | H |
| 2.081 | Me | —SMe | 4-Me-phenyl | H |
| 2.082 | n-Pr | —SMe | 4-Me-phenyl | H |
| 2.083 | Et | —SMe | pyrazol-1-yl | H |
| 2.084 | Me | —SMe | pyrazol-1-yl | H |
| 2.085 | n-Pr | —SMe | pyrazol-1-yl | H |
| 2.086 | Et | —SMe | furan-3-yl | H |
| 2.087 | Me | —SMe | furan-3-yl | H |
| 2.088 | n-Pr | —SMe | furan-3-yl | H |
| 2.089 | Et | —SMe | 3,5-dimethyl-isoxazol-4-yl | H |
| 2.090 | Me | —SMe | 3,5-dimethyl-isoxazol-4-yl | H |
| 2.091 | n-Pr | —SMe | 3,5-dimethyl-isoxazol-4-yl | H |
| 2.092 | Et | —SMe | thien-2-yl | H |
| 2.093 | Me | —SMe | thien-2-yl | H |
| 2.094 | n-Pr | —SMe | thien-2-yl | H |
| 2.095 | Et | —SMe | 1-methyl-pyrazol-4-yl | H |
| 2.096 | Me | —SMe | 1-methyl-pyrazol-4-yl | H |
| 2.097 | n-Pr | —SMe | 1-methyl-pyrazol-4-yl | H |
| 2.098 | Et | —SMe | pyrimidin-5-yl | H |
| 2.099 | Me | —SMe | pyrimidin-5-yl | H |
| 2.100 | n-Pr | —SMe | pyrimidin-5-yl | H |
| 2.101 | Et | —SMe | pyridin-3-yl | H |
| 2.102 | Me | —SMe | pyridin-3-yl | H |
| 2.103 | n-Pr | —SMe | pyridin-3-yl | H |
| 2.104 | Et | —S(O)₂Me | phenyl | H |
| 2.105 | n-Pr | —S(O)₂Me | phenyl | H |
| 2.106 | Et | —S(O)₂Me | 4-Cl-phenyl | H |
| 2.107 | Me | —S(O)₂Me | 4-Cl-phenyl | H |
| 2.108 | n-Pr | —S(O)₂Me | 4-Cl-phenyl | H |
| 2.109 | Et | —S(O)₂Me | 4-F-phenyl | H |
| 2.110 | Me | —S(O)₂Me | 4-F-phenyl | H |
| 2.111 | n-Pr | —S(O)₂Me | 4-F-phenyl | H |
| 2.112 | Et | —S(O)₂Me | 4-MeS(O)₂-phenyl | H |
| 2.113 | Me | —S(O)₂Me | 4-MeS(O)₂-phenyl | H |
| 2.114 | n-Pr | —S(O)₂Me | 4-MeS(O)₂-phenyl | H |
| 2.115 | Et | —S(O)₂Me | 4-MeS-phenyl | H |
| 2.116 | Me | —S(O)₂Me | 4-MeS-phenyl | H |
| 2.117 | n-Pr | —S(O)₂Me | 4-MeS-phenyl | H |
| 2.118 | Et | —S(O)₂Me | 4-Me-phenyl | H |
| 2.119 | Me | —S(O)₂Me | 4-Me-phenyl | H |
| 2.120 | n-Pr | —S(O)₂Me | 4-Me-phenyl | H |
| 2.121 | Et | —S(O)₂Me | pyrazol-1-yl | H |
| 2.122 | Me | —S(O)₂Me | pyrazol-1-yl | H |
| 2.123 | n-Pr | —S(O)₂Me | pyrazol-1-yl | H |
| 2.124 | Et | —S(O)₂Me | furan-3-yl | H |
| 2.125 | Me | —S(O)₂Me | furan-3-yl | H |
| 2.126 | n-Pr | —S(O)₂Me | furan-3-yl | H |
| 2.127 | Et | —S(O)₂Me | 3,5-dimethyl-isoxazol-4-yl | H |
| 2.128 | Me | —S(O)₂Me | 3,5-dimethyl-isoxazol-4-yl | H |
| 2.129 | n-Pr | —S(O)₂Me | 3,5-dimethyl-isoxazol-4-yl | H |
| 2.130 | Et | —S(O)₂Me | thien-2-yl | H |

TABLE 2-continued

Examples of herbicidal compounds of the present invention.

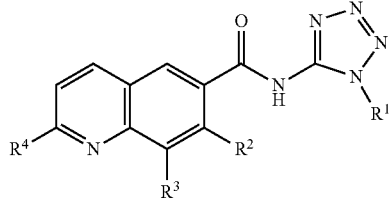
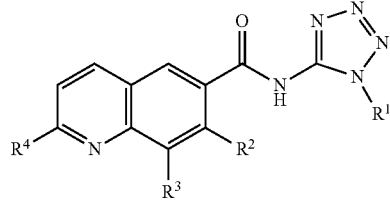

| Compound | R¹ | R² | R³ | R⁴ |
|---|---|---|---|---|
| 2.131 | Me | —S(O)₂Me | thien-2-yl | H |
| 2.132 | n-Pr | —S(O)₂Me | thien-2-yl | H |
| 2.133 | Et | —S(O)₂Me | 1-methyl-pyrazol-4-yl | H |
| 2.134 | Me | —S(O)₂Me | 1-methyl-pyrazol-4-yl | H |
| 2.135 | n-Pr | —S(O)₂Me | 1-methyl-pyrazol-4-yl | H |
| 2.136 | Et | —S(O)₂Me | pyrimidin-5-yl | H |
| 2.137 | Me | —S(O)₂Me | pyrimidin-5-yl | H |
| 2.138 | n-Pr | —S(O)₂Me | pyrimidin-5-yl | H |
| 2.139 | Et | —S(O)₂Me | pyridin-3-yl | H |
| 2.140 | Me | —S(O)₂Me | pyridin-3-yl | H |
| 2.141 | n-Pr | —S(O)₂Me | pyridin-3-yl | H |
| 2.142 | Et | CF₃ | phenyl | Me |
| 2.143 | n-Pr | CF₃ | phenyl | Me |
| 2.144 | Et | CF₃ | 4-Cl-phenyl | Me |
| 2.145 | Me | CF₃ | 4-Cl-phenyl | Me |
| 2.146 | n-Pr | CF₃ | 4-Cl-phenyl | Me |
| 2.147 | Et | CF₃ | 4-F-phenyl | Me |
| 2.148 | Me | CF₃ | 4-F-phenyl | Me |
| 2.149 | n-Pr | CF₃ | 4-F-phenyl | Me |
| 2.150 | Et | CF₃ | 4-MeS(O)₂-phenyl | Me |
| 2.151 | Me | CF₃ | 4-MeS(O)₂-phenyl | Me |
| 2.152 | n-Pr | CF₃ | 4-MeS(O)₂-phenyl | Me |
| 2.153 | Et | CF₃ | 4-MeS-phenyl | Me |
| 2.154 | Me | CF₃ | 4-MeS-phenyl | Me |
| 2.155 | n-Pr | CF₃ | 4-MeS-phenyl | Me |
| 2.156 | Et | CF₃ | 4-Me-phenyl | Me |
| 2.157 | Me | CF₃ | 4-Me-phenyl | Me |
| 2.158 | n-Pr | CF₃ | 4-Me-phenyl | Me |
| 2.159 | Et | CF₃ | pyrazol-1-yl | Me |
| 2.160 | Me | CF₃ | pyrazol-1-yl | Me |
| 2.161 | n-Pr | CF₃ | pyrazol-1-yl | Me |
| 2.162 | Et | CF₃ | furan-3-yl | Me |
| 2.163 | Me | CF₃ | furan-3-yl | Me |
| 2.164 | n-Pr | CF₃ | furan-3-yl | Me |
| 2.165 | Et | CF₃ | 3,5-dimethyl-isoxazol-4-yl | Me |
| 2.166 | Me | CF₃ | 3,5-dimethyl-isoxazol-4-yl | Me |
| 2.167 | n-Pr | CF₃ | 3,5-dimethyl-isoxazol-4-yl | Me |
| 2.168 | Et | CF₃ | thien-2-yl | Me |
| 2.169 | Me | CF₃ | thien-2-yl | Me |
| 2.170 | n-Pr | CF₃ | thien-2-yl | Me |
| 2.171 | Et | CF₃ | 1-methyl-pyrazol-4-yl | Me |
| 2.172 | Me | CF₃ | 1-methyl-pyrazol-4-yl | Me |
| 2.173 | n-Pr | CF₃ | 1-methyl-pyrazol-4-yl | Me |
| 2.174 | Et | CF₃ | pyrimidin-5-yl | Me |
| 2.175 | Me | CF₃ | pyrimidin-5-yl | Me |
| 2.176 | n-Pr | CF₃ | pyrimidin-5-yl | Me |
| 2.177 | Et | CF₃ | pyridin-3-yl | Me |
| 2.178 | Me | CF₃ | pyridin-3-yl | Me |
| 2.179 | n-Pr | CF₃ | pyridin-3-yl | Me |
| 2.180 | Et | Cl | phenyl | Me |
| 2.181 | Me | Cl | phenyl | Me |
| 2.182 | n-Pr | Cl | phenyl | Me |
| 2.183 | Et | Cl | 4-Cl-phenyl | Me |
| 2.184 | Me | Cl | 4-Cl-phenyl | Me |
| 2.185 | n-Pr | Cl | 4-Cl-phenyl | Me |
| 2.186 | Et | Cl | 4-F-phenyl | Me |
| 2.187 | Me | Cl | 4-F-phenyl | Me |
| 2.188 | n-Pr | Cl | 4-F-phenyl | Me |
| 2.189 | Et | Cl | 4-MeS(O)₂-phenyl | Me |
| 2.190 | Me | Cl | 4-MeS(O)₂-phenyl | Me |
| 2.191 | n-Pr | Cl | 4-MeS(O)₂-phenyl | Me |
| 2.192 | Et | Cl | 4-MeS-phenyl | Me |
| 2.193 | Me | Cl | 4-MeS-phenyl | Me |
| 2.194 | n-Pr | Cl | 4-MeS-phenyl | Me |
| 2.195 | Et | Cl | 4-Me-phenyl | Me |
| 2.196 | Me | Cl | 4-Me-phenyl | Me |
| 2.197 | n-Pr | Cl | 4-Me-phenyl | Me |
| 2.198 | Et | Cl | pyrazol-1-yl | Me |
| 2.199 | Me | Cl | pyrazol-1-yl | Me |
| 2.200 | n-Pr | Cl | pyrazol-1-yl | Me |
| 2.201 | Et | Cl | furan-3-yl | Me |
| 2.202 | Me | Cl | furan-3-yl | Me |
| 2.203 | n-Pr | Cl | furan-3-yl | Me |
| 2.204 | Et | Cl | 3,5-dimethyl-isoxazol-4-yl | Me |
| 2.205 | Me | Cl | 3,5-dimethyl-isoxazol-4-yl | Me |
| 2.206 | n-Pr | Cl | 3,5-dimethyl-isoxazol-4-yl | Me |
| 2.207 | Et | Cl | thien-2-yl | Me |
| 2.208 | Me | Cl | thien-2-yl | Me |
| 2.209 | n-Pr | Cl | thien-2-yl | Me |
| 2.210 | Et | Cl | 1-methyl-pyrazol-4-yl | Me |
| 2.211 | Me | Cl | 1-methyl-pyrazol-4-yl | Me |
| 2.212 | n-Pr | Cl | 1-methyl-pyrazol-4-yl | Me |
| 2.213 | Et | Cl | pyrimidin-5-yl | Me |
| 2.214 | Me | Cl | pyrimidin-5-yl | Me |
| 2.215 | n-Pr | Cl | pyrimidin-5-yl | Me |
| 2.216 | Et | Cl | pyridin-3-yl | Me |
| 2.217 | Me | Cl | pyridin-3-yl | Me |
| 2.218 | n-Pr | Cl | pyridin-3-yl | Me |
| 2.219 | Et | —SMe | phenyl | Me |
| 2.220 | Me | —SMe | phenyl | Me |
| 2.221 | n-Pr | —SMe | phenyl | Me |
| 2.222 | Et | —SMe | 4-Cl-phenyl | Me |
| 2.223 | Me | —SMe | 4-Cl-phenyl | Me |
| 2.224 | n-Pr | —SMe | 4-Cl-phenyl | Me |
| 2.225 | Et | —SMe | 4-F-phenyl | Me |
| 2.226 | Me | —SMe | 4-F-phenyl | Me |
| 2.227 | n-Pr | —SMe | 4-F-phenyl | Me |
| 2.228 | Et | —SMe | 4-MeS(O)₂-phenyl | Me |
| 2.229 | Me | —SMe | 4-MeS(O)₂-phenyl | Me |
| 2.230 | n-Pr | —SMe | 4-MeS(O)₂-phenyl | Me |
| 2.231 | Et | —SMe | 4-MeS-phenyl | Me |
| 2.232 | Me | —SMe | 4-MeS-phenyl | Me |
| 2.233 | n-Pr | —SMe | 4-MeS-phenyl | Me |
| 2.234 | Et | —SMe | 4-Me-phenyl | Me |
| 2.235 | Me | —SMe | 4-Me-phenyl | Me |
| 2.236 | n-Pr | —SMe | 4-Me-phenyl | Me |
| 2.237 | Et | —SMe | pyrazol-1-yl | Me |
| 2.238 | Me | —SMe | pyrazol-1-yl | Me |
| 2.239 | n-Pr | —SMe | pyrazol-1-yl | Me |
| 2.240 | Et | —SMe | furan-3-yl | Me |
| 2.241 | Me | —SMe | furan-3-yl | Me |
| 2.242 | n-Pr | —SMe | furan-3-yl | Me |
| 2.243 | Et | —SMe | 3,5-dimethyl-isoxazol-4-yl | Me |
| 2.244 | Me | —SMe | 3,5-dimethyl-isoxazol-4-yl | Me |
| 2.245 | n-Pr | —SMe | 3,5-dimethyl-isoxazol-4-yl | Me |
| 2.246 | Et | —SMe | thien-2-yl | Me |
| 2.247 | Me | —SMe | thien-2-yl | Me |
| 2.248 | n-Pr | —SMe | thien-2-yl | Me |
| 2.249 | Et | —SMe | 1-methyl-pyrazol-4-yl | Me |
| 2.250 | Me | —SMe | 1-methyl-pyrazol-4-yl | Me |
| 2.251 | n-Pr | —SMe | 1-methyl-pyrazol-4-yl | Me |
| 2.252 | Et | —SMe | pyrimidin-5-yl | Me |
| 2.253 | Me | —SMe | pyrimidin-5-yl | Me |
| 2.254 | n-Pr | —SMe | pyrimidin-5-yl | Me |
| 2.255 | Et | —SMe | pyridin-3-yl | Me |
| 2.256 | Me | —SMe | pyridin-3-yl | Me |
| 2.257 | n-Pr | —SMe | pyridin-3-yl | Me |
| 2.258 | Et | —S(O)₂Me | phenyl | Me |
| 2.259 | Me | —S(O)₂Me | phenyl | Me |
| 2.260 | n-Pr | —S(O)₂Me | phenyl | Me |

TABLE 2-continued

Examples of herbicidal compounds of the present invention.

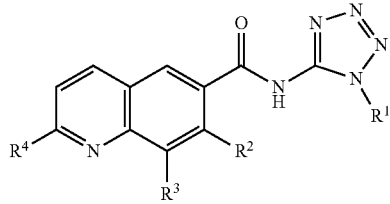

| Compound | R¹ | R² | R³ | R⁴ |
|---|---|---|---|---|
| 2.261 | Et | —S(O)₂Me | 4-Cl-phenyl | Me |
| 2.262 | Me | —S(O)₂Me | 4-Cl-phenyl | Me |
| 2.263 | n-Pr | —S(O)₂Me | 4-Cl-phenyl | Me |
| 2.264 | Et | —S(O)₂Me | 4-F-phenyl | Me |
| 2.265 | Me | —S(O)₂Me | 4-F-phenyl | Me |
| 2.266 | n-Pr | —S(O)₂Me | 4-F-phenyl | Me |
| 2.267 | Et | —S(O)₂Me | 4-MeS(O)₂-phenyl | Me |
| 2.268 | Me | —S(O)₂Me | 4-MeS(O)₂-phenyl | Me |
| 2.269 | n-Pr | —S(O)₂Me | 4-MeS(O)₂-phenyl | Me |
| 2.270 | Et | —S(O)₂Me | 4-MeS-phenyl | Me |
| 2.271 | Me | —S(O)₂Me | 4-MeS-phenyl | Me |
| 2.272 | n-Pr | —S(O)₂Me | 4-MeS-phenyl | Me |
| 2.273 | Et | —S(O)₂Me | 4-Me-phenyl | Me |
| 2.274 | Me | —S(O)₂Me | 4-Me-phenyl | Me |
| 2.275 | n-Pr | —S(O)₂Me | 4-Me-phenyl | Me |
| 2.276 | Et | —S(O)₂Me | pyrazol-1-yl | Me |
| 2.277 | Me | —S(O)₂Me | pyrazol-1-yl | Me |
| 2.278 | n-Pr | —S(O)₂Me | pyrazol-1-yl | Me |
| 2.279 | Et | —S(O)₂Me | furan-3-yl | Me |
| 2.280 | Me | —S(O)₂Me | furan-3-yl | Me |
| 2.281 | n-Pr | —S(O)₂Me | furan-3-yl | Me |
| 2.282 | Et | —S(O)₂Me | 3,5-dimethyl-isoxazol-4-yl | Me |
| 2.283 | Me | —S(O)₂Me | 3,5-dimethyl-isoxazol-4-yl | Me |
| 2.284 | n-Pr | —S(O)₂Me | 3,5-dimethyl-isoxazol-4-yl | Me |
| 2.285 | Et | —S(O)₂Me | thien-2-yl | Me |
| 2.286 | Me | —S(O)₂Me | thien-2-yl | Me |
| 2.287 | n-Pr | —S(O)₂Me | thien-2-yl | Me |
| 2.288 | Et | —S(O)₂Me | 1-methyl-pyrazol-4-yl | Me |
| 2.289 | Me | —S(O)₂Me | 1-methyl-pyrazol-4-yl | Me |
| 2.290 | n-Pr | —S(O)₂Me | 1-methyl-pyrazol-4-yl | Me |
| 2.291 | Et | —S(O)₂Me | pyrimidin-5-yl | Me |
| 2.292 | Me | —S(O)₂Me | pyrimidin-5-yl | Me |
| 2.293 | n-Pr | —S(O)₂Me | pyrimidin-5-yl | Me |

TABLE 2-continued

Examples of herbicidal compounds of the present invention.

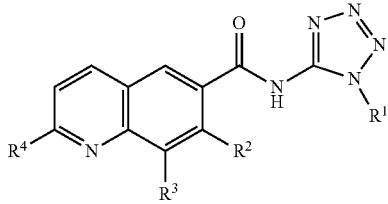

| Compound | R¹ | R² | R³ | R⁴ |
|---|---|---|---|---|
| 2.294 | Et | —S(O)₂Me | pyridin-3-yl | Me |
| 2.295 | Me | —S(O)₂Me | pyridin-3-yl | Me |
| 2.296 | n-Pr | —S(O)₂Me | pyridin-3-yl | Me |

BIOLOGICAL EXAMPLES

Experiment B1

Seeds of a variety of test species are sown in standard soil in pots (*Lolium perenne* (LOLPE), *Solanum nigrum* (SOLNI), *Amaranthus retoflexus* (AMARE), *Setaria faberi* (SETFA), *Echinochloa crus-galli* (ECHCG), *Ipomoea hederacea* (IPOHE)). After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds are applied at 1000 g/h. The test plants are then grown in a glasshouse under controlled conditions in a glasshouse (at 24/16° C., day/night; 14 hours light; 65% humidity) and watered twice daily. After 13 days for pre and post-emergence, the test is evaluated for the percentage damage caused to the plant. The biological activities are shown in the following table on a five point scale (5=80-100%; 4=60-79%; 3=40-59%; 2=20-39%; 1=0-19%).

| | POST Application | | | | | | PRE Application | | | | | |
|---|---|---|---|---|---|---|---|---|---|---|---|---|
| Compound | LOLPE | SOLNI | AMARE | SETFA | ECHCG | IPOHE | LOLPE | SOLNI | AMARE | SETFA | ECHCG | IPOHE |
| 1.001 | 5 | 5 | 5 | 5 | 5 | 5 | 5 | 5 | 5 | 5 | 5 | 5 |
| 1.002 | 5 | 5 | 5 | 5 | 5 | 5 | 5 | 5 | 5 | 5 | 5 | 5 |
| 1.003 | 1 | 5 | 5 | 2 | 3 | 4 | 1 | 5 | 5 | 1 | 5 | 2 |
| 1.007 | 5 | 5 | 5 | 5 | 5 | 5 | 5 | 5 | 5 | 5 | 5 | 5 |
| 1.009 | 4 | 5 | 5 | 5 | 5 | 5 | 5 | 5 | 5 | 5 | 5 | 5 |
| 1.010* | 4 | 5 | 5 | 5 | 5 | 5 | 2 | 5 | 5 | 2 | 5 | 4 |
| 1.011 | 5 | 5 | 5 | 5 | 5 | 5 | 5 | 5 | 5 | 5 | 5 | 5 |
| 1.017 | 4 | 5 | 5 | 5 | 5 | 5 | 4 | 5 | 5 | 5 | 5 | 5 |
| 1.030 | 4 | 5 | 5 | 5 | 5 | 5 | 4 | 5 | 5 | 5 | 5 | 4 |
| 1.031 | 5 | 5 | 5 | 5 | 5 | 5 | 5 | 5 | 5 | 5 | 5 | 5 |
| 1.032 | 5 | 5 | 5 | 5 | 5 | 5 | 5 | 5 | 5 | 5 | 5 | 5 |
| 1.033 | 1 | 5 | 5 | 2 | 2 | 5 | 1 | 4 | 5 | 1 | 1 | 3 |
| 1.034 | 4 | 5 | 5 | 5 | 5 | 5 | 5 | 5 | 5 | 5 | 5 | 5 |
| 1.035 | 4 | 5 | 5 | 5 | 5 | 5 | 5 | 5 | 5 | 5 | 5 | 5 |
| 1.036 | 4 | 5 | 5 | 5 | 5 | 5 | 4 | 5 | 5 | 5 | 5 | 5 |
| 1.037 | 5 | 5 | 5 | 5 | 5 | 5 | 3 | 5 | 5 | 5 | 5 | 4 |
| 1.038 | 5 | 5 | 5 | 5 | 5 | 5 | 4 | 5 | 5 | 5 | 5 | 4 |
| 1.045* | 3 | 5 | 5 | 5 | 5 | 5 | 1 | 4 | 4 | 1 | 4 | 2 |

*Applied at 250 g/ha

Experiment B2

A comparative test is performed to compare the efficacy of quinoline compounds of the present invention with quinoline compounds taught in WO2014/037342 and napthyridines taught in WO2013/092834. Seeds of a variety of test species were sown in standard soil in pots. After cultivation for one day (pre-emergence) or after 10 days cultivation (post-emergence) under controlled conditions in a glasshouse (at 24/16° C., day/night; 14 hours light; 65% humidity), the plants were sprayed with an aqueous spray solution derived from the formulation of the technical active ingredient in 0.6 ml acetone and 45 ml formulation solution containing 10.6% Emulsogen EL (Registry number 61791-12-6), 42.2% N-methyl pyrrolidone, 42.2% dipropylene glycol monomethyl ether (CAS RN 34590-94-8) and 0.2% X-77 (CAS RN 11097-66-8).

The test plants were then grown in a glasshouse under controlled conditions in a glasshouse (at 24/16° C., day/night; 14 hours light; 65% humidity) and watered twice daily. After 14 days for post-emergence and 21 days for pre-emergence and phytotoxicity evaluated using a five point scale (5=80-100%; 4=60-79%; 3=40-59%; 2=20-39%; 1=0-19%). Test Plants:—*Eriochloa villosa* (ERBVI), *Panicum miliaceum* (PANMI).

| Compound | POST Application (60 g/ha) | | PRE Application (250 g/ha) | |
|---|---|---|---|---|
| | ERBVI | PANMI | ERBVI | PANMI |
| Compound 1.001 | 5 | 5 | 3 | 5 |
| Compound 2.002 WO2013/092834 | 1 | 2 | 1 | 1 |
| Compound 43-3 WO2014/037342 | 1 | 1 | 1 | 2 |

This result shows that the quinoline compounds of the present invention exhibit a surprisingly improved herbicidal effect, when applied either pre- or post-emergence, compared to known, structurally similar compounds.

The invention claimed is:
1. A compound of Formula (I):

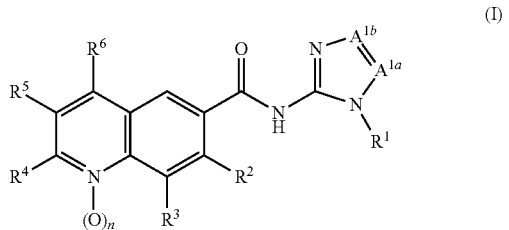

(I)

or an agronomically acceptable salt thereof,
wherein:—
$A^{1a}$ and $A^{1b}$ are independently selected from CH and N, wherein $A^{1a}$ and $A^{1b}$ are not both CH;
$R^1$ is selected from the group consisting of $C_1$-$C_6$-alkyl-, $C_1$-$C_6$-alkoxy-$C_1$-$C_3$-alkyl-, $C_1$-$C_6$-haloalkoxy-$C_1$-$C_3$-alkyl-, $C_1$-$C_6$-haloalkyl-, $C_2$-$C_6$-alkenyl-, $C_2$-$C_6$-haloalkenyl-, $C_2$-$C_6$-alkynyl-, $C_2$-$C_6$-haloalkynyl-, heteroaryl-, ($C_3$-$C_7$)-cycloalkyl-, heterocyclyl- and phenyl-, wherein the heteroaryl-, ($C_3$-$C_7$)-cycloalkyl-, heterocyclyl- and phenyl- are optionally substituted by one or more substituents selected from the group consisting of halogen, nitro, cyano, $C_1$-$C_6$-alkyl-, $C_1$-$C_6$-haloalkyl-, $C_3$-$C_6$-cycloalkyl-, $C_1$-$C_6$alkyl-S(O)p-, $C_1$-$C_3$-alkoxy- and $C_1$-$C_6$alkoxy-$C_1$-$C_4$alkyl-;
$R^2$ is selected form the group consisting of $C_1$-$C_6$alkyl-, $C_1$-$C_6$alkoxy-, $C_1$-$C_6$ haloalkyl-, $C_1$-$C_6$haloalkoxy-, $C_1$-$C_6$alkoxy-$C_1$-$C_6$alkyl-, $C_1$-$C_3$ alkoxy-$C_2$-$C_3$ alkoxy-$C_1$-$C_3$ alkyl-, $C_1$-$C_3$ alkoxy-$C_{1-3}$-haloalkyl-, $C_1$-$C_3$-alkoxy-$C_1$-$C_3$-alkoxy-$C_1$-$C_3$-haloalkyl-, halogen, cyano, nitro, $C_1$-$C_6$alkyl-S(O)p-, $C_1$-$C_6$haloalkyl-S(O)$_p$—, $C_4$-$C_6$-oxasubstituted-cycloalkoxy-$C_1$-$C_3$alkyl-, $C_4$-$C_6$-oxasubstituted-cycloalkoxy-$C_1$-$C_3$-haloalkyl-, ($C_1$-$C_3$-alkanesulfonyl-$C_1$-$C_3$ alkylamino)-$C_1$-$C_3$ alkyl- and ($C_1$-$C_3$ alkanesulfonyl-$C_3$-$C_4$cycloalkylamino)-$C_1$-$C_3$ alkyl-;
$R^3$ is aryl or a 5 or 6-membered heteroaryl, the heteroaryl containing one to three heteroatoms each independently selected from the group consisting of oxygen, nitrogen and sulphur, and wherein the aryl or heteroaryl component may be optionally substituted by one or more substituents selected from the group consisting of halogen, $C_1$-$C_6$alkyl-, $C_2$-$C_6$alkenyl-, $C_2$-$C_6$alkynyl-, $C_1$-$C_6$haloalkyl-, $C_1$-$C_6$alkoxy-, $C_1$-$C_6$alkoxyC_1$-$C_3$alkyl-, $C_1$-$C_6$alkoxyC_1$-$C_3$ alkoxy-, $C_1$-$C_6$haloalkoxy-, $C_1$-$C_6$alkyl- S(O)p-, —NR$^{7a}$R$^{7b}$, cyano and nitro;
$R^4$ is selected from the group consisting of hydrogen, halogen, hydroxyl, sulfhydryl, $C_1$-$C_6$alkyl-, $C_3$-$C_6$cycloalkyl-, $C_1$-$C_6$haloalkyl-, $C_2$-$C_6$haloalkenyl-, $C_2$-$C_6$alkenyl, $C_3$-$C_6$alkynyl, $C_1$-$C_6$alkoxy, $C_4$-$C_7$cycloalkoxy-, $C_1$-$C_6$haloalkoxy-, $C_1$-$C_6$alkyl- S(O)p-, $C_1$-$C_6$alkoxy-$C_1$-$C_6$alkyl-, $C_1$-$C_6$alkoxy-$C_2$-$C_6$alkoxy- and $C_1$-$C_6$alkoxy-$C_2$-$C_6$alkoxy-$C_1$-$C_6$-alkyl-;
$R^5$ is selected from the group consisting of hydrogen, halogen, $C_1$-$C_6$alkyl- and $C_1$-$C_6$haloalkyl-;
$R^6$ is selected from the group consisting of hydrogen, methyl and halogen;
$R^{7a}$ and $R^{7b}$ are independently selected from the group consisting of hydrogen and $C_1$-$C_6$alkyl or together form a $C_4$-$C_5$ alkylene chain;
n=0 or 1; and
p=0, 1 or 2.
2. The compound according to claim 1, wherein $A^{1a}$ and $A^{1b}$ are N.
3. The compound of claim 1, wherein $R^1$ is selected from the group consisting of methyl, ethyl and n-propyl.
4. The compound of claim 1, wherein $R^2$ is selected form the group consisting of $C_1$-$C_6$alkyl-, $C_1$-$C_6$alkoxy-, $C_1$-$C_6$ haloalkyl-, halogen and $C_1$-$C_6$alkyl-S(O)p-.
5. The compound of claim 1, wherein $R^3$ is an aryl or heteroaryl selected from the group consisting of phenyl, furanyl, thiophenyl, thiazolyl, oxazolyl, isoxazolyl, thiazolyl, pyrazolyl, isothiazolyl, pyridyl, pyridazinyl, pyrazinyl, pyrimidinyl and triazolyl.
6. The compound according to claim 5, wherein $R^3$ is phenyl.
7. The compound of claim 1, wherein $R^4$ is selected from the group consisting of hydrogen, $C_1$-$C_6$alkyl- and $C_1$-$C_6$haloalkyl-.
8. The compound of claim 1, wherein $R^5$ is hydrogen or halogen.
9. A herbicidal composition comprising a compound according to claim 1 and an agriculturally acceptable formulation adjuvant.

10. The herbicidal composition according to claim 9, further comprising at least one additional pesticide.

11. The herbicidal composition according to claim 10, wherein the additional pesticide is a herbicide.

12. The method of controlling weeds at a locus comprising application to the locus of a weed controlling amount of a composition according to claim 9.

* * * * *